United States Patent [19]

Ishikawa et al.

[11] Patent Number: 5,650,153

[45] Date of Patent: Jul. 22, 1997

[54] RECOMBINANT MAREK'S DISEASE VIRUS AND VACCINE

[75] Inventors: Toyokazu Ishikawa; Sadao Manabe, both of Mitoyo-gun; Chisato Mori, Kanonji; Akihisa Takamizawa, Kanonji; Iwao Yoshida, Kanonji; Juichiro Osame, Mitoyo-gun; Keisuke Takaku, Toyono-gun; Konosuke Fukai, Toyonaka, all of Japan

[73] Assignee: The Research Foundation for Microbial Diseases, Osaka, Japan

[21] Appl. No.: 293,337

[22] Filed: Aug. 24, 1994

Related U.S. Application Data

[63] Continuation of Ser. No. 948,469, Sep. 22, 1992, abandoned, which is a continuation of Ser. No. 324,064, Mar. 16, 1989, abandoned.

[30] Foreign Application Priority Data

Mar. 20, 1988 [JP] Japan ................................ 63-66973
Sep. 14, 1988 [JP] Japan ................................ 63-230851

[51] Int. Cl.$^6$ .................... A61K 39/265; C12N 15/86
[52] U.S. Cl. .................... 424/229.1; 435/320.1
[58] Field of Search ................ 435/320.1, 69.1, 435/172.1, 172.3, 235.1; 424/93.2, 93.6

[56] References Cited

FOREIGN PATENT DOCUMENTS

WO87/00862  2/1987  WIPO.
WO87/04463  7/1987  WIPO.
WO88/07088  9/1988  WIPO.

OTHER PUBLICATIONS

Van Zaane et al., "Molecular–Biological Characterization of Marek's Disease Virus", Virology, vol. 121, pp. 133–146, 1982.

Gibbs, Carol P. et al. "Extensive Homology Exitst Between Marek Disease Herpesvirus and Its Vaccine Virus, Herpesvirus of Turkeys." *Proceedings of the National Academy of Sciences of The United States of America*, vol. 81, No. 11(Jun. 1984), pp. 3365–3369.

Silva, Robert F. et al. "Genomic Expansion of Marek's Disease Virus DNA Is Associated with Serial In Vitro Passage." *Journal of Virology*, vol. 54, No. 3(Jun. 1985), pp. 690–696.

Advances in Virus Research, vol. 30, pp. 225–277 (1985).

Bio/Technology, vol. 6, pp. 47–55 (1988).

Journal of Virology, vol. 51, pp. 102–109 (1984).

Journal of Virology, vol. 57, pp. 464–474 (1986).

Virology, vol. 157, pp. 351–358 (1987).

Journal of Virology, vol. 61, pp. 2614–2620 (1987).

*Primary Examiner*—David Guzo
*Attorney, Agent, or Firm*—Armstrong, Westerman, Hattori, McLeland & Naughton

[57] ABSTRACT

There is provided a recombinant Marek's disease virus comprising the genomic DNA of an attenuated Marek's disease virus and a foreign gene from another source. The present recombinant virus can advantageously be used as an active ingredient for a multifunctional live vaccine, exhibiting not only the antigenicity and immunogenicity of the Marek's disease virus but also the properties ascribed to the foreign gene. Since the suitable host cell for the recombinant virus of the present invention is an avian cell which is available in a large quantity and not expensive, the recombinant virus of the present invention can be produced efficiently at low cost on a commercial scale.

10 Claims, 29 Drawing Sheets

FIG. 3(a)

```
                1        6       16       26       36   46
MDV                                                TGCCTATGTAGTGAAATCTATACTGGGATTTATCATAACTAGTTTA
HVT   AATATCGGCGTTACTAATAAGGTGTCACAAATTGGCAGCAGAGCCAGTGTCGTGAAATC 56       66       76       86       96  106
MDV   CTTGTTTGTATATTAGTAGCGCTATCTTGACCAAATCGTTGTTCACATCTTGGTCATATA
HVT   TGTACTGGGCTTCATTATTCCGGGATGCTTACTTGCCTGTGCTATTACCACTATCGTGATA 116      126      136      146      156  166
MDV   CGTATTGACCGTTGTTTCGAACCGCGAATAAAACTTCATACATACTAAACGATGGAGTT
HVT   GATCGTCGGTCTGCGCATCGCCCATGCTGGGCGAACGCTCTTTCGAACCGTGAATAAAAC 176      186      196      206      216  226
MDV   GTGTTTTATGAGCGGTGAAAACAAAGGTACCATCGGTTAAAACTAAGTTGCATATCGTA
HVT   TTTGTATCTACTAAACAATAACTTTGTGTTTTATTGAGCGGTCGAAAACAATGAGGAGCT 236      246      256      266      276  286
MDV   ATCCACAAAAATCATTTTATACATCATCCCGAAGAGAGACACCAAACGTAACCCTCTACATA
HVT   GCAATTTAAAGCTAACCGCATACGCCCGGGCGGGTAAAGACCATTTTATACCATATTACGC
```

FIG. 3 (b)

```
             296        306        316        326        336        346
MDV   TCTTCCCTCATGCTCACGCCGCGGTGTGTTACGAGCTTTGGGGTGGACTTGGACTCTTTTT
         MetLeuThrProArgValLeuArgAlaLeuGlyTrpThrGlyLeuPhePhe

HVT   ATCTATCGAAACTTGTTCGAGAACCGCAAGTATATGTTTCCAACATGGCGTTCTACCG
                                  MetValSerAsnMetArgValLeuPro 356        366        376        386        396        406
      TTGCTTTTATCTCCGAGCAACGTCCTAGGAGCCAGCCTTAGCCGGGATCTCGAAACACCC
      LeuLeuSerProSerAsnValLeuGlyAlaSerLeuSerArgAspLeuGluThrPro
               ***                                       ******
      GACTGCGCTCGACGGGGATGGGGTGGGCATATTTCTAGTTCTGTCTTTACAGCAAACCTCT
      AspCysAlaArgArgAspGlyValGlyIlePheLeuValLeuSerLeuGlnThrSer 416        426        436        446        456        466
      CCATTTCTATCCTTTGATCCATCCAACATTCAATTAACGGCGCCTTAACTGAGGTA
      ProPheLeuSerProPheAspProSerAsnIleSerIleAsnGlyAlaProLeuThrGluVal
      TGTGCCGGATTGCCCCATAACGTCGATACCCATCATATCCTAACTTCAACCCTTCTCCC
      CysAlaGlyLeuProHisAsnValAspThrHisHisIleLeuThrPheAsnProSerPro 476        486        496        506        516        526
      CCTCATGGACCTTCCACAGAAAGTGTCAACAAATTCGGAAAGTACCAATGAACATACC
      ProHisGlyProSerThrGluSerValSerThrAsnSerGluSerThrAsnGluHisThr
                                                            ***
      ATTTCGGCCGATGGCGTTCCTTGTCAGAGGTGCCCAATTCGCCTACGACCGAATTATCT
      IleSerAlaAspGlyValProLeuSerGluValProAsnSerProThrGluLeuSer
```

FIG. 3(c)

```
        536        546        556        566        576        586
ATAACAGAAACGACGGCAAGAACGCATACATCCACAACAATGCTGTCTACGGACAAGCAA
IleThrGluThrGlyLysAsnAlaTyrIleHisAsnAsnAlaSerThrAspLysGln
                           ***                           ***
ACAACTGTCGCCACCAAGACAGCTGTACCGACGACTGAAAGCACTGAAGCACTAGTTCCTCCGAAGCG
ThrThrValAlaThrLysThrAlaValProThrThrGluSerThrSerSerGluAla 596        606        616        626        636        646
AATGGGAACGACACTCATAAAATGCCCAATATACTCTGCGATACGGAAGAAGTTTTGTT
AsnAlaAsnAspThrHisLysMetProAsnIleLeuCysAspThrGluValPheVal
***           ******                  ***                 **************
CACCGCAACTCTTCTCACAAAATACCTGATATAATCTGCGAGAAGAAGTATTCGTA
HisArgAsnSerHisLysIleProAspIleIleCysAspArgGluValPheVal 656        666        676        686        696        706
TTCCTTAACGAAACGGGAAGATTTGTTTGTACTCTCAAAGTCGACCCCCTCGGATAGT
PheLeuAsnGluThrGlyArgPheValCysThrLeuLysValAspProProSerAspSer
***************  ***    ***    **************************
TTCCTTAACAATACAGGAAGAATTTTGTGTGACCTTATAGTCGACCCCCTTCAGACGAT
PheLeuAsnAsnThrGlyArgIleLeuCysAspLeuIleValAspProProSerAspAsp
```

FIG. 3 (d)

```
           716          726          736          746          756          766
GAATGGTCCAACTTTGTTCTAGATCTTAACCCAATTGAATACCACGCCAACGAA
GluTrpSerAsnPheValLeuAspLeuIlePheAsnProIleGluTyrHisAlaAsnGlu
*************************      ****************************
GAATGGTCCAACTTCGCTCTTGACGTCACGTTCAATCCAATCGAATACCACGCCAACGAA
GluTrpSerAsnPheAlaLeuAspValThrPheAsnProIleGluTyrHisAlaAsnGlu 776          786          796          806          816          826
AAGAATGTGGAAGCGGCGTATCGCTGGTCTCTATGGAGTCCCGGATCAGATCAGATATGCA
LysAsnValGluAlaAlaArgIleAlaGlyLeuTyrGlyValProGlySerAspTyrAla
***************      ****************************************
AAGAATGTAGAGAGGTTGCCCGAGTGCCGGTCTATACGGAGTACCGGGGTCGATTATGCA
LysAsnValGluValAlaArgValAlaGlyLeuTyrGlyValProGlySerAspTyrAla 836          846          856          866          876          886
TACCCACGTCAATCTGAATTAATTTCTTCGATTCGAGAGATCCCCAGGCACATTTGG
TyrProArgGlnSerGluLeuIleSerSerIleArgArgAspProGlnGlyThrPheTrp
***      *****************************************      ******
TACCCTAGGAAATCGGAATTAATATCCTCCATTCGACGGGATCCCCAGGGTTCTTTCTGG
TyrProArgLysSerGluLeuIleSerSerIleArgArgAspProGlnGlySerPheTrp
```

FIG. 3 (e)

```
            896         906         916         926         936         946
ACGAGCCCATCACCCTCATGGAAAACAAGTACTTCATATGGATAAACAAAACAACCAATACG
ThrSerProSerProHisGlyAsnLysTyrPheIleTrpIleAsnLysThrThrAsnThr
*********   ***  ****************   *******************   ***
ACTAGTCCTACACCCCGTGGAAATAAATATTTCATATGGATTAATAAAACAATGCACACC
ThrSerProThrProArgGlyAsnLysTyrPheIleTrpIleAsnLysThrMetHisThr 956         966         976         986         996        1006
ATGGGCGTGGAAATTAGAGAAATGTAGATTATGCTGATAATGGCTACATGCAAGTCATTATG
MetGlyValGluIleArgGluMetValAspTyrAlaAspAsnGlyTyrMetGlnValIleMet
************  *********   *************   ****************
ATGGGCGTGGAAGTTAGAGAAATGTCGACTACAAAGACAACGGCTACTTTCAAGTGATACTG
MetGlyValGluValArgGluMetSerThrThrLysAspAsnGlyTyrPheGlnValIleLeu 1016        1026        1036        1046        1056        1066
CGTGACCATTTTAATCGGCCCTTTAATAGATAAACATATTTACATTACGTGTGTGTCAACGA
ArgAspHisPheAsnArgProLeuIleAspLysHisIleTyrIleArgValCysGlnArg
*******                   ****************************** **
CGTGATAGATTTAATCGCCCATTGGTAGAAAAACATATTTACATGCGTGTGTGCCAACGA
ArgAspArgPheAsnArgProLeuValGluLysHisIleTyrMetArgValCysGlnArg
```

FIG. 3 (f)

```
      1076       1086       1096       1106       1116       1126
CCTGCATCAGTGGATGTACTGGCCCCTCCAGTCCTCAGCGGAGAAAATTACAAGGCATCT
ProAlaSerValAspValLeuAlaProProValLeuSerGlyGluAsnTyrLysAlaSer
************************************************************
CCCGCATCCGTGGATGTATTGGCCCCTCCAGTTCTCAGCGGAGAAAACTACAAGCATCT
ProAlaSerValAspValLeuAlaProProValLeuSerGlyGluAsnTyrLysAlaSer 1136       1146       1156       1166       1176       1186
TGTATCGTTAGACACTTTATCCCCCTGGATCTGTCTATGTATCTTGGAGACAGAATGGA
CysIleValArgHisPheTyrProProGlySerValTyrValSerTrpArgGlnAsnGly
*******************************************       *********
TGCATCGTTAGACATTTTATCCCCGGGATCTGTCTACGTATCTTGGAGACGTAACGGA
CysIleValArgHisPheTyrProProGlySerValTyrValSerTrpArgArgAsnGly 1196       1206       1216       1226       1236       1246
AACATTGCAACTCCTCGGAAAGATCGGCGATGGAAGTTTTGGTGGTTCGAATCTGGTAGA
AsnIleAlaThrProArgLysAspArgLysAspArgGlySerPheTrpTrpPheGluSerGlyArg
******        **********************************************
AACATTCCCACACCCCGCAAAGACCGTGACGGAGTTTTTGGTGGTTCGAATCTGGCCGC
AsnIleProThrProArgLysAspArgLysAspArgGlySerPheTrpTrpPheGluSerGlyArg
```

FIG. 3 (g)

```
      1256       1266       1276       1286       1296       1306
GGAGCTACGTTGGTTTCTACAATAACATTGGGAAATTCAGGAATTGATTTCCCCCAAA
GlyAlaThrLeuValSerThrIleThrLeuGlyAsnSerGlyIleAspPheProProLys
************************************************* **********
GGAGCCACATTAGTATCCACAATAACCCTCGGAAACTCTGGACTCGAATCTCCTCCAAAG
GlyAlaThrLeuValSerThrIleThrLeuGlyAsnSerGlyLeuGluSerProProLys 1316       1326       1336       1346       1356       1366
ATATCTTGTCTGGTTGCCTGGAAGCCAGGGTGATATGATCAGCACGACGAATGCCACAGCT
IleSerCysLeuValAlaTrpLysGlnGlyAspMetIleSerThrThrAsnAlaThrAla
**************************** *****************************
GTTTCCTGCTTGGTAGCGTGGAGGCAAGGCGATATGATAAGCACATGAATGCTACAGCT
ValSerCysLeuValAlaTrpArgGlnGlyAspMetIleSerThrSerAsnAlaThrAla 1376       1386       1396       1406       1416       1426
ATCCCGACGGTATATCATCATCCCCGTTTATCCCTGGCTTTAAAGATTTCAAGGGTATGCAATA
IleProThrValTyrHisHisProArgLeuSerLeuAlaPheLysAspGlyTyrAlaIle
************************ ****** ****************************
GTACCGACGGTATATTATTATCACCCCCGTATCCTGGCATTTAAAGATGGGTATGCAATA
ValProThrValTyrTyrHisProArgIleSerLeuAlaPheLysAspGlyTyrAlaIle
```

FIG. 3 (h)

```
            1436        1446        1456        1466        1476        1486
TGTACTATAGAATGTGTCCCCTCTGAGATTACTGTAGGTGGTTAGTAGTACATGATGAAGCG
CysThrIleGluCysValProSerGluIleThrValArgTrpLeuValHisAspGluAla
       ****************************************************
TGTACTATAGAATGTGTCCCCTCTGGATTACTGTGAGGTGGTTAGTTCATGATGAACCC
CysThrIleGluCysValProSerGlyPheThrValArgTrpLeuValHisAspGluPro 1496        1506        1516        1526        1536        1546
CAGCCTAACACAACTTATAATACTGTGGTTACAGGTCTCTGCCGGACCATCGATCGCCAT
GlnProAsnThrThrTyrAsnThrValValThrGlyLeuCysArgThrIleAspArgHis
       ****************************************************
CAGCCTAACACAACTTATGATACTGTGGTTACAGGTCTCTGCAGGACCATCGATCGTTAT
GlnProAsnThrThrTyrAspThrValValThrGlyLeuCysArgThrIleAspArgTyr 1556        1566        1576        1586        1596        1606
AGAAATCTCCCTCAGCCGCATTCCAGTATGGGACAATTGGACGAAAACAAAATATACGTGC
ArgAsnLeuSerArgIleProIleProValTrpAspAsnTrpThrLysThrLysTyrThrCys
   ***************          ****  ****************************
AGAAATCTCGCCAGTCCGGATTCCAGTCCAGGACAACTGGGCGAAAACGAAGTATACGTGC
ArgAsnLeuAlaSerArgIleProIleProValGlnAspAsnTrpAlaLysThrLysTyrThrCys
```

FIG. 3(i)

```
        1616       1626       1636       1646       1656       1666
AGACTCATAGGCTACCCCTTCGATGAAGATAAATTCAAGATTCGAATATTACGATGCA
ArgLeuIleGlyTyrProPheAspGluAspLysPheGlnAspSerGluTyrTyrAspAla
**********************************  ***  ********************
AGACTAATTGGATATCCGTTCGACGTGGATAGATTCAAAAATTCGAATATTATGATGCA
ArgLeuIleGlyTyrProPheAspValAspArgPheGlnAsnSerGluTyrTyrAspAla 1676       1686       1696       1706       1716       1726
ACTCCATCTGCAAGAGGAACACCCATGGTTATTACGGTTACGGCAGTTTTGGGATTGGCT
ThrProSerAlaArgGlyThrProMetValIleThrValThrAlaValLeuGlyLeuAla
****************************  ***  **************************
ACGCCGTCGGCAAGAGGAATGCCGATGATTGTAACAATTACGGCCGTTCTAGGACTGGCC
ThrProSerAlaArgGlyMetProMetIleValThrIleThrAlaValLeuGlyLeuAla 1736       1746       1756       1766       1776       1786
GTAATTTTAGGGATGGGGATAATCATGACTGCCCTATGTTTATACACTCCACACGAAAAA
ValIleLeuGlyMetGlyIleIleMetThrAlaLeuCysLeuTyrThrProHisGluLys
*********  ****************  *****************  ***  ***
TTGTTTTAGGTATTGGTATCATTATCACAGCCCTATGCTTTACCTACCGGGGGGAAT
LeuPheLeuGlyIleGlyIleIleIleThrAlaLeuCysPheTyrLeuProGlyArgAsn
```

FIG. 3 (j)

```
              1796      1806      1816      1826      1836      1846
MDV   ATATTCGATTATAATCTCATTGTTATGTGTAGTTGTGATTTATTAAACATATTTTTATAAC
      IlePheAspTyrAsnLeuIleValMet 1856      1866      1876      1886      1896      1906
HVT   TAAGATTAACCATCGTATGTGATATAAAAATTATTAAGTGTTATAACCGATCGCATTCTT 1916      1926      1936      1946      1956      1966
      TCTAGTATTCTCCGAGTTACTTATATATTTATTTGTCAGACAATAAATGCAATAGTGGAGA 1976      1986      1996      2006      2016      2026
      CTGTTTCGATTCACAATAAATAAAAATGGTATTGTAATCAACCACCATCGCATTGTTTCGTA

AACGTGAGGGGAGTCTGTAAACAGAATACGTATAATCATCTATTGAATAAAAAGATTGTG

GATGACTCATGTTCAATCCGCGTGATGTCAAAAATACGTATTTTGGTATCACGAGCGGC

GTATAAATGAAGATAGCAGCAAGTCATTCCAAGCTCTCCATTCTATTTAAACAATGTACA

CAAAATGCCCATTATGTTATTTTAC
```

FIG. 3 (k)

```
             2036      2046      2056      2066      2076      2086
MDV  GTTTAAAGTTAGATATTTTAGGATAGAAATTAACATTGTCCCACAATGAGTAATCATGTC 2096      2106      2116      2126      2136      2146
     CACTTCGGCTAGTACCAAAGGCGAGATGATCGTGCCAGTCACCACAATATTTCATATCGA 2156      2166      2176      2186      2196      2206
     AACAATAATCTATCACTTTGTCATGGAGATATCGTCGACATACGTATTATTAGCACTGTA 2216      2226      2236      2246      2256      2266
     TACGGTATCTCTCTTTCGTATATCAGATAGATGATATACGTCACAGACTAGCGTCCATGAAA 2276      2286      2296      2306      2316      2326
     CAGAAAACTGATACAAATACTGGCAATCCGTCACTTTTAAGAGGTAATATCTCCGTCGGGG 2336      2346      2356      2366      2376
     TGAGTGTATAGACTCTGTCAACGCATTTCTTAGCCTTTTAAGAATT
```

```
         10         20         30         40         50         60
ATGGACCGTGCAGTTAGCAGAGTTGTGCTAGAGAATGAAGAAAGAGAAGCACGGAACACA
METAspArgAlaValSerArgValValLeuGluAsnGluGluArgGluAlaArgAsnThr 70         80         90        100        110        120
TGGCGCTTGGTCTTCCGGATCGCAGTTTTACTTTTAATAGTAATGACTTTAGCTATCTCT
TrpArgLeuValPheArgIleAlaValLeuLeuIleValMETThrLeuAlaIleSer 130        140        150        160        170        180
GTAGCCTCCCTGGTATACACGATGGGGCTAGTACGCCGCGGCACCTCGTAGGCATATCG
ValAlaSerLeuValTyrThrMETGlyAlaSerThrProArgHisLeuValGlyIleSer 190        200        210        220        230        240
ACTGTGATCTCTAAGACAGAGACAAGATTACGTCTCTTACTCAGTTCAAATCAAGATGTA
ThrValIleSerLysThrGluThrArgLeuArgLeuLeuThrGlnIleLysAspVal 250        260        270        280        290        300
GTAGATAGGATATATAAGCAGGTGGCCCTTGAATCTCCGCTGGCCGCTAAATACTGAA
ValAspArgIleTyrLysGlnValAlaLeuGluSerProLeuAlaLeuLeuAsnThrGlu 310        320        330        340        350        360
TCTATAATTATGAATGCAATAACGTCTCTCTTATCAAATTAACGGGGCTGCGAATAAT
SerIleIleMETAsnAlaIleThrSerLeuSerTyrGlnIleAsnGlyAlaAlaAsnAsn 370        380        390        400        410        420
AGCAGGTGTGGGGGCCGCTGTTCATGACCGGATTATATCGGGGGGATAGGCAAAGAACTC
SerArgCysGlyAlaAlaValHisAspProAspTyrIleGlyIleGlyIleLysGluLeu 430        440        450        460        470        480
ATAGTAGACGACACTAGTGATGTCACATCATTCTATCCTTCTGCATACCAAGAACACCTG
IleValAspAspThrSerAspValThrSerPheTyrProSerAlaTyrGlnGluHisLeu
```

FIG. 5 (b)

```
        490              500             510             520             530             540
AATTTTATCCCGGGGCCTACTACAGGATCAGGTTGCACTCGGATACCCTCATTTGACATG
AsnPheIleProAlaProThrThrGlySerGlyCysThrArgIleProSerPheAspMET 550              560             570             580             590             600
AGTGCTACCCACTACTGTTATACTCACAATGTGATATTGTCTGGTTGCAGAGATCACTCA
SerAlaThrHisTyrCysTyrThrHisAsnValIleLeuSerGlyCysArgAspHisSer 610              620             630             640             650             660
CACTCACATCAATACTTAGCACTTGGTGTGCTTCAGACACATCTGCAACAGGGAGGGTATTC
HisSerHisGlnTyrLeuAlaLeuGlyValLeuGlnThrSerAlaThrGlyArgValPhe 670              680             690             700             710             720
TTTCTACTCTGCGTTCCATCAATTTAGATGACAACCAAAATCGGAAGTCCTGCAGTGTG
PheSerThrLeuArgSerIleAsnLeuAspAspAsnGlnAsnArgLysSerCysSerVal 730              740             750             760             770             780
AGTGCAACTCCTCTAGGTTGTGATATGCTTCTAAAGTCACAGAGACTGAGGAAGAG
SerAlaThrProLeuGlyCysAspMETLeuCysSerLysValThrGluThrGluGluGlu 790              800             810             820             830             840
GATTATAAGTCAGTTACCCCCACATCAATGGTGCACGGAAGGTTAGGGTTTGACGGTCAA
AspTyrLysSerValThrProThrSerMETValHisGlyArgLeuGlyPheAspGlyGln 850              860             870             880             890             900
TACCATGAGAAGGACTTAGACATCGCAGTCTTATTTAAGGATTGGGTGGCAAATTACCCG
TyrHisGluLysAspLeuAspIleAlaValLeuPheLysAspTrpValAlaAsnTyrPro 910              920             930             940             950             960
GGAGTGGGAGGTGGGTCTTTTATTGACGACCGCGTATGGTTCCCAGTTACGGAGGGCTA
GlyValGlyGlyGlySerPheIleAspAspArgValTrpPheProValTyrGlyGlyLeu
```

FIG. 5 (c)

```
          970       980       990      1000      1010      1020
AAACCTAATTCGCCTAGGCGACACTGCACAAGAAGGAAATATGTAATATACAAGCGCTAT
LysProAsnSerProSerAspThrAlaGlnGluGlyLysTyrValIleTyrLysArgTyr 1030      1040      1050      1060      1070      1080
AATAACACATGCCCCGATGAACAAGATTACCAAATCCGGATGGTTAAGTCTTCGTACAAG
AsnAsnThrCysProAspGluGlnAspTyrGlnIleArgMETValLysSerSerTyrLys 1090      1100      1110      1120      1130      1140
CCTGGGCGGTTCGGTGGAAAGCGGGTACAGCAAGCCATCTTATCTATCAAAGTGTCAACA
ProGlyArgPheGlyGlyLysArgValGlnAlaIleLeuSerIleLysValSerThr 1150      1160      1170      1180      1190      1200
TCCTTGGGCGAGGACCCGGTGTCAACTGTTCCGCCTAATACAGTTACACTCATGGGGGCC
SerLeuGlyGluAspProValSerThrValProProAsnThrValThrLeuMETGlyAla 1210      1220      1230      1240      1250      1260
GAAGAGAGTTCTCACAGTAGGACATCTCATTTCTTGTACCAACGAGGGTCTTCATATAGT
GluGluSerSerHisSerHisPheLeuTyrGlnArgGlySerSerTyr 1270      1280      1290      1300      1310      1320
TTCTCCCCTGCCTTATTATATCCTATGACAGTCTATAACAAAACAACTACTCTTCATAGT
PheSerProAlaLeuTyrProMETThrValTyrAsnLysThrThrThrLeuHisSer 1330      1340      1350      1360      1370      1380
CCTTATACATTTAATGCTTTCACCCGGCCAGGTAGTGTCCCTTGTCAGGCATCAGCAAGA
ProTyrThrPheAsnAlaPheThrArgProGlySerValProCysGlnAlaSerAlaArg 1390      1400      1410      1420      1430      1440
TGCCCTAACTCATGTATCACTGGAGTCTATACTGATCCGTATCCTTTAGTCTTCCATAGG
CysProAsnSerCysIleThrGlyValTyrThrAspProTyrProLeuValPheHisArg
```

FIG. 5 (d)

```
          1450       1460       1470       1480       1490       1500
    AATCATATACCTTGCGAGGGTCTTCGGGACAATGCTTGATGATGAACAAGCAAGACTCAAT
    AsnHisThrLeuArgGlyValPheGlyThrMetLeuAspAspGluGlnAlaArgLeuAsn 1510       1520       1530       1540       1550       1560
    CCCGTATCCGCAGTATTCGATAACATATCCCGGAGTCGTGTAACCCGGGTAAGTTCAAGC
    ProValSerAlaValPheAspAsnIleSerArgSerArgValThrArgValSerSerSer 1570       1580       1590       1600       1610       1620
    AGTACCAAGGCAGCATACACGACATCGACATGTTTTAAGGTTGTCAAGACCAATAAAGCT
    SerThrLysAlaAlaTyrThrThrSerThrCysPheLysValValLysThrAsnLysAla 1630       1640       1650       1660       1670       1680
    TATTGTCTTAGCATTGCAGAAATATCCAATACCCTATTCGGGAATTCAGGATCGTTCCT
    TyrCysLeuSerIleAlaGluIleIleSerAsnThrLeuPheGlyGluPheArgIleValPro 1690       1700       1710       1720       1730       1740
    TTACTAGTTGAGATTCTTAAGGATGATAGGGTTTAAGAAGGCTAGATCTGGTCGGTTGAG
    LeuLeuValGluIleLeuLysAspAspArgVal 1750       1760       1770       1780       1790       1800
    TCGAACACAGGAGTTGGTTGGGGGATGATGTGTATCACCTATCTCTCACAATGCAAAGGA

1805
    TCAAA
```

RECOMBINANT MAREK'S DISEASE VIRUS AND VACCINE

This application is a continuation of application Ser. No. 07/948,469 filed Sep. 22, 1992, now abandoned which in turn is a continuation of application Ser. No. 07/324,064 filed Mar. 16, 1989, abandoned.

BACKGROUND OF THE INVENTION

1. Field of the Invention

This invention relates to a recombinant Marek's disease virus. More particularly, the present invention is concerned with a recombinant Marek's disease virus comprising an attenuated Marek's disease virus and a foreign gene which does not inherently exist in the attenuated Marek's virus. The recombinant virus of the present invention can advantageously be used as an active ingredient for a multifunctional live vaccine, namely a live vaccine having not only the anti-genicity and immunogenicity of the Marek's disease virus but also the properties ascribed to the foreign gene. Further, since the suitable host cell for the recombinant virus of the present invention is an avian cell which is available in a large quantity and not expensive, the recombinant virus of the present invention can be produced efficiently on a commercial scale at low cost.

2. Discussion of Related Art

Marek's disease is a viral lymphoproliferative disease which is highly contagious and spreads mainly in young chicken flocks. The disease had been recognized as a kind of lymphoid leukemia, but in 1961 Biggs distinguished this disease from leukemia of chicken and named it "Marek's disease" after the the name of the discoverer, Marek, who was first to report this disease.

The Marek's disease virus is a DNA virus having an envelope and is classified into Gallid herpes-virus 1 or Gallid herpes-virus 2 belonging to the subfamily *Gammaherpesvirinae* in the family *Herpes-viridae* (Intervirology, Vol. 17, pp. 47–51, S. Kerger, 1982). The diameter of a mature virus particle of this virus, including an envelope, is about 150 to 180 nm. The virus is comprised of an envelope and a nucleocapsid contained therein. The nucleocapsid has a shape of regular icosahedron having a diameter of about 100 nm. In the center of the nucleocapsid, there exists a nucleoid having a toroidal structure of a diameter of about 50 to 60 nm and containing a straight double-stranded DNA having a molecular weight of about $1.0 \times 10^8$. The virus attacks 12 to 20-week age chicks to cause a paresis and a spastic or atonic paralysis due to the lesion of nerves, and causes tumors. The Marek's disease prevails quickly and the mortality by this disease is extremely high. Therefore, the economical damage caused by this disease is very large. In order to prevent this disease, a Marek's disease virus live vaccine has broadly been used in the field of the poultry raising for about 10 years. The Marek's disease virus is classified into the following three serotypes according to the results of a fluoroimmunoassay, an agar gel immunodiffusion and a virus neutralization test (Advances in Virus Research, Vol. 30, pp. 225–277, Academic Press, INC., 1985; and The Herpesvirus, Vol. 1, ed. B. Roizman, pp. 333–431, Plenum Press, 1982).

Type I: a virulent strain of Marek's disease virus (hereinafter referred to as "MDV") which is pathogenic and tumourigenic to chickens and causes various symptoms in chickens, and an attenuated strain of the above-mentioned virulent MDV, which is nonpathogenic and obtained by artificial mutation of the above-mentioned virulent strain cultured in a cell culture in vitro;

Type II: a wild attenuated strain of Marek's disease virus; and

Type III: a herpesvirus of turkeys (hereinafter referred to as "HVT") nonpathogenic to chickens.

The term "attenuated Marek's disease virus" used herein means any one of the attenuated MDV strain of Type I, the wild attenuated MDV strain of Type II, and the HVT of Type III.

Heretofore, various virus vectors have been reported since around 1979. For example, reference may be made to Nature (London), 277, 108–114 (1979); ibid., 278, 35–40 (1979), in which the production of rabbit β-globin by the use of an SV40 vector is reported. In 1980, the World Health Organization (WHO) declared, in the general meeting, the success in extermination of the smallpox in the world and counseled the abolishment of vaccination because of the danger that some persons who received vaccination are killed due to its adverse effect. Since then, with respect to possible utilities of vaccinia virus in other fields, many studies have been made. For example, the use of the vaccinia virus as a cloning vector and an expression vector has been studied and reported [Proceedings of The National Academy of Sciences, U.S.A., 79, 4927–4931 (1982); and ibid., 79, 7415–7419 (1982)]. Thereafter, the Special Advisory Group in WHO proposed a project for promoting the research of a recombinant vaccine by the use of a virus vector derived from a vaccinia virus etc. [Nature (London), 312, 299 (1984)]. Since the above-mentioned declaration and proposal of WHO, fundamental study on and development of various virus vectors have broadly been made [Virus, 36, 1–41 (1986) and ibid., 37, 1–40 (1987)]. Heretofore, it has been reported that, for example, a papillomavirus, a polyomavirus, an adenovirus, a vaccinia virus, a retrovirus, a baculovirus, a parvovirus, a cauliflower mosaic virus and a tobacco mosaic virus can be used as a cloning vector or an expression vector for a foreign gene. With respect to the production of a useful substance by the use of a virus vector as mentioned above, reference may be made to, for example, the following publications:

Use of an attenuated vaccinia virus vector: European Patent Application Publication Specification No. 83286 (production of various antigens), PCT Patent Application Publication No. WO84/02077 (production of various antigens), Japanese Patent Application Laid-Open Specification No. 61-289888 (production of an antigen of a malarial parasite), Japanese Patent Application Laid-Open Specification No. 62-44178 (production of a hepatitis B virus surface antigen), Japanese Patent Application Laid-Open Specification No. 62-151186 (production of a feline leukemia virus antigen), Japanese Patent Application Laid-Open Specification No. 62-294698 (production of a melanoma antigen), Japanese Translation Publication No. 63-500003 of PCT Patent Application (production of γ-interferon) and Japanese Translation Publication No. 63-500005 of PCT Patent Application (production of human interleukin 2);

Use of a nonpathogenic adenovirus vector: PCT Patent Application Publication No. WO83/02393 (production of a polyomavirus antigen) and Japanese Patent application Laid-Open Specification No. 63-12296 (production of a protein such as C-peptide);

Use of a bovine rotavirus vector: PCT Patent Application Publication No. WO85/00184 (production of a human rotavirus antigen);

Use of a virulent herpes simplex virus type 1 vector: Japanese Patent Application Laid-Open Specification No. 61-1390 (production of a hepatitis B virus surface antigen)

and Japanese Patent Application Laid-Open Specification No. 62-257385 (preparation of an attenuated recombinant virus comprising virulent herpes simplex viruses types 1 and 2);

Use of a long terminal repeat (LTR) vector derived from a retrovirus: Japanese Translation Publication No. 61-502932 of PCT Patent Application (amplification of the production of a tumor specific antigen);

Use of an attenuated varicella virus vector: Japanese Patent Application Laid-Open Specification No. 63-12277 (production of an Epstein-Barr virus antigen); and Use of a tobacco mosaic virus vector: Japanese Patent Application Laid-Open Specification No. 63-14693 (transformation of a higher plant cell).

However, the above-mentioned techniques are still only at the stage of experiment with respect to production of biological preparations, including vaccines, because not only do not these conventional techniques give satisfactory yields and purities of intended products, but also the safety and effect of the products on a human being, a domestic fowl, a domestic animal and a pet have not been confirmed. Therefore, any biological preparations produced by using a conventional virus vector have not yet been approved officially and put to practical use. For example, with respect to a vaccinia virus vector, the vector can be used for producing various useful substances as mentioned above. However, the vaccinia virus vector is disadvantageous in that the vector is inherently neuro-pathogenic and therefore has the danger of causing serious adverse effects, e.g., the danger of induction of postvaccinal encephalitis. Accordingly, the safety of the vaccinia virus vector and product obtained by means of the vector is uncertain. Further, it should be noted that since there are not a few persons and animals that have already acquired the immunity against the vaccinia virus and have antibodies against the virus, when the recombinant vaccinia virus containing a foreign gene is administered as a live vaccine to such a person or animal, the multiplication of the recombinant vaccinia virus, that is, the multiplication of the foreign gene, in a human or animal body, which is required to attain a sufficient effect of immunization, is disadvantageously suppressed or prevented. Therefore, it is not always expected to attain the desired effect of the recombinant virus as a multifunctional live vaccine having not only the antigenicity and immunogenicity of the vaccinia virus but also the properties ascribed to the foreign gene. In other words, the subjects to whom the administration of the recombinant vaccinia virus is effective are limited and, therefore, such a recombinant vaccinia virus containing the foreign gene cannot always be used as an effective live vaccine.

Further, there has also been tentatively conducted the production of various substances by means of a recombinant virus comprising, as a vector, the genome of baculovirus, e.g., of *Autographa califomia* nuclear polyhedrosis virus which is capable of infecting lepidopteran insects [Bio/Technology, Vol. 8, No. 6, pp. 47–55, (1988)]. Examples of substances produced by the recombinant baculovirus include about 35 kinds of antigens and enzymes, for example, human interferons α and β, human interleukin 2, parainfluenza virus hemagglutinin-neuraminidase, influenza virus hamagglutinin, various antigens of AIDS virus, hepatitis B virus surface antigen, *Escherichia coli* β-galactosidase and the like. However, the production of the above-mentioned products using the baculovirus must be conducted in a limited type of culture host, namely an insect cell, and the safety and effect of the products on humans or animals have not yet been confirmed. Further, the suitability of the vector for use in producing the desired substances on a commercial scale has not been considered. Moreover, since the host cell of the above-mentioned recombinant vaculovirus is an insect cell which is not available in a large quantity and is expensive, the desired substances cannot be produced by the recombinant vaculovirus on a commercial scale at low cost.

From the foregoing, it is apparent that a recombinant virus which can be safely produced on a large scale and can advantageously be used as an active ingredient for a multifunctional live vaccine with safety has heretofore not been developed, and it has been earnestly desired to overcome the above-mentioned disadvantages of the conventional recombinant virus vectors.

SUMMARY OF THE INVENTION

The present inventors have made extensive and intensive studies with a view toward developing a recombinant virus which has none of the disadvantages of the conventional recombinant viruses as mentioned above. As a result, it has unexpectedly been found that when the genomic DNA of an attenuated Marek's disease virus is used as a virus vector to prepare a recombinant virus comprising the genomic DNA and a foreign gene, the resultant recombinant virus is extremely stable and free from the danger of reverse mutation to a virulent virus. Therefore, the resultant recombinant virus can be used as a safe and effective live vaccine which has not only the antigenicity and immunogenicity of the Marek's disease virus, but also additional properties derived from the foreign gene recombined therewith. Further, it has also been found that the production of a recombinant virus can be conducted safely without biohazard. When a gene coding for an antigen other than those present in the attenuated MDV is used as a foreign gene to be recombined with the MDV genomic DNA, the resultant recombinant virus has the antigens of both the attenuated MDV and the foreign gene and, therefore, the recombinant virus as such can be used as a multifunctional live vaccine. Such a multifunctional live vaccine can be produced by single multiplication of the above-mentioned recombinant virus. The production of the multifunctional live vaccine is simple and less expensive as compared to the production of the conventional multifunctional vaccine because for producing the conventional multifunctional vaccines, it is usually necessary to conduct multiplication of plural types of viruses individually. Furthermore, when the recombinant virus is cultured, an animal cell, particularly an avian cell of a primary culture or about the 2nd to 5th subculture can be used as a host. Such a cell can be obtained on a large scale at low cost. Therefore, the recombinant virus can be produced on a large scale at low cost. Furthermore, the above-mentioned host cell is free of an unidentified carcinogenic substance and any other harmful substances, differing from a cell strain or an established cell line resulting from mutagenesis. Therefore, there is no danger that the resultant recombinant virus is contaminated with such a carcinogenic or harmful substance. Based on the above-mentioned findings, the present invention has been completed.

It is, therefore, an object of the present invention to provide a novel recombinant virus, which is useful as an active ingredient for a multi-functional live vaccine.

It is another object of the present invention to provide a multifunctional Marek's disease live vaccine comprising a recombinant virus of the kind as mentioned above.

It is a further object of the present invention to provide a method for producing a multifunctional Marek's disease live vaccine comprising a recombinant virus of the kind as mentioned above.

BRIEF DISCUSSION OF THE DRAWINGS

In the Drawings:

FIG. 3 (parts a to k) shows the whole nucleotide sequences of the gA antigen genes of MDV C2 strain and HVTO1) strain, and the amino acid sequences encoded thereby;

FIG. 4 shows a flow chart indicating the cloning of a gene coding for hemagglutinin and neuraminidase (hereinafter referred to as "HN") of a Newcastle disease virus (hereinafter referred to as "NDV"), and the construction of plasmid pHN-1 containing the gene;

FIG. 5 (parts a to d) shows the whole nucleotide sequence of the structural gene coding for HN of NDV, and the amino acid sequence encoded thereby;

Figure 20:
Figure 21:

FIG. 20 is a photograph showing the result obtained by subjecting QEF cells infected with recombinant virus strain MDV C2R to immunoassay by indirect immunofluorescence technique in which anti-MDV gA antigen chicken antiserum is used as a primary antibody; and FIG. 21 shows a photograph showing the result obtained by subjecting QEF cells infected with recombinant virus strain MDV C2R to immunoassay by indirect immunofluorescence technique in which anti-NDV NH chicken antiserum is used as a primary antibody.

DETAILED DESCRIPTION OF THE INVENTION

Essentially, according to the present invention, there is provided a recombinant Marek's disease virus comprising the genomic DNA of an attenuated Marek's disease virus and at least one foreign gene derived from another source, wherein said foreign gene is inserted in said genomic DNA in a correct reading frame downstream of at least one promoter of said genomic DNA, which promoter is functional in a host cell for expressing said foreign gene, said recombinant Marek's disease virus having an antigenicity and immunogenicity of a Marek's disease virus and containing a polypeptide encoded by said foreign gene.

As mentioned before, the attenuated Marek's disease viruses (MDV) used in the present invention is defined as an attenuated MDV of Type I, a wild attenuated MDV of Type II and a herpesvirus of turkeys (HVT) of Type III. It is preferred that a strain customarily used for the production of a Marek's disease live vaccine be used as the attenuated MDV, because such a strain was confirmed with respect to its safety and effect, and the use of such a strain has been approved by the authorities of various countries. Examples of attenuated MDV's include MDV (chicken virus) C2 strain [Gan Monograph on Cancer Research, 10, 91–107 (1971)], HVT (turkey virus) O1 strain [The Journal of Japanese Society of Veterinary, 27, 20–24 (1974)], and the like. The use of the above-mentioned strains have been approved by the Ministry of Agriculture, Forestry and Fisheries, Japan and they are commercially available. For example, the MDV C2 strain and the HVT O1 strain are manufactured and sold as attenuated Marek's disease live vaccines by The Research Foundation for Microbial Diseases of Osaka University, Japan in the tradenames of BIKEN "C2" strain and BIKEN "O1" strain. The MDV C2 strain and HVT O1 strain are also deposited at the European Collection of Animal Cell Cultures (ECACC), United Kingdom, under accession numbers V89030814 and V89030815, respectively. The attenuated MDV used in the present invention, of course, is not restricted to the above-mentioned strains, and any attenuated MDV strains can be used.

The term "genomic DNA" of the attenuated MDV used herein means the entire DNA which the attenuated MDV contains.

As the foreign gene, any gene which is exogenous to the genomic DNA of the attenuated MDV may be used. For example, there may be used a gene coding for a polypeptide selected from the group consisting of antigens, enzymes, peptide hormones and structural proteins derived from or produced by viruses other than the attenuated Marek's disease virus, chlamydia, rickettsia, mycoplasmas, bacteria, protozoa, animal cells or plant cells. Representative examples of foreign genes include genes coding for a protective antigen, hemagglutinin, neuraminidase and the like, which are derived from Ibaraki disease virus, bovine viral diarrhea-mucosal disease virus, infectious bovine rhinotracheitis virus, bovine ephemeral fever disease virus, rinderpest virus, adenovirus type 7, rotavirus, equine influenza virus, foot-and-mouth disease virus, hog cholera virus, porcine parvovirus, fowlpox virus, pigeon pox virus, Newcastle disease virus, infectious laryngotracheitis virus, avian encephalomyelitis virus, avian infectious bronchitis virus, infectious canine adenovirus, distemper virus, feline panleukopenia virus, feline leukemia virus, mink enteritis virus, rabies virus, pseudorabies virus, infectious bursal disease virus, influenza virus, parainfluenza virus, poliomyelitis virus, Japanese encephalitis virus, virus of hemorrhagic fever with renal syndrome, yellow fever virus, cytomegalovirus, chickenpox virus, mumps virus, measles virus, rubella virus, hepatitis B virus, adult T cell leukemia virus, AIDS virus and the like; genes coding for a toxin, a structural protein, an enzyme, a protective antigen, a hemagglutin, a physiologically active substance and the like, which are derived from pathogenic bacteria such as *Bordetella bronchiseptica, Haemophilus paragallinarum* A, *Leptospira canicola, Leptospira icterohaemorrhagica*, and other pathogenic bacteria causing diseases such as blackleg, anthrax, swine erysipelas, botulinum C, cholera, diphteria, tetanus, tuberculosis, gas gangrene, pneumonia, paratyphoid, typhoid fever, typhus and meningitis. However, the foreign gene which may be used in the present invention is not restricted to those mentioned above.

According to the present invention, at least one foreign gene may be inserted in the genomic DNA of the attenuated MDV. The foreign gene is inserted in the genomic DNA in a correct reading frame downstream of a promoter of the genomic DNA of the attenuated MDV. In the genomic DNA of the attenuated MDV, there are different types of promoters, which individually control different types of genes of the genomic DNA. With respect to the genes of the genomic DNA of the attenuated MDV, 40 to 50 types of genes have already been identified by immune precipitation using SDS-polyacrylamide gel electrophoresis. It is known that these genes code for different types of proteins having molecular weights of from 19,000 to 350,000. The region of each of the above-mentioned genes is under the control of a promoter. Therefore, in order to express the foreign gene, any portion in each of the above-mentioned structural genes can be utilized as a portion in which the foreign gene is inserted. However, from the standpoint of high frequency of expression of the gene it is preferred to insert a foreign gene in a position downstream of a promoter of the gene selected from a glycoprotein A antigen (gA antigen) gene, a glycoprotein B antigen (hereinafter referred to as "gB antigen") gene, an antigen C gene, a gene coding for a DNA-binding protein having a molecular weight of about 135,000, genes coding for major virus-specific proteins respectively having molecular weights of about 86,000 and about 92,000, and genes coding for phosphorylated proteins respectively having molecular weights of about 36,000, about 39,000 and about 44,000. With respective to those genes, reference may be made to "Advances in Virus Research", 30, 225–277, Academic Press, Inc. 1985).

The recombinant virus of the present invention can be prepared by a method comprising the steps of:

a) ligating a DNA fragment obtained by cleavage of a genomic DNA of an attenuated Marek's disease virus with a restriction enzyme to a replicable vector to form a first replication vector;

b) inserting at least one foreign gene sequence in the DNA fragment of the first replication vector to form a second replication vector;

c) cotransfecting a cell with the second replication vector and an attenuated Marek's disease virus;

d) incubating the cotransfected cell for a time sufficient for homologous recombination to occur between the DNA fragment of the second replication vector containing the DNA fragment of Marek's disease virus genome together with the foreign gene and a portion of the genomic DNA of the attenuated Marek's disease virus having a homologous or similar nucleotide sequence to the DNA fragment; and e) isolating from the cell a recombinant virus comprising an attenuated Marek's disease virus and a foreign gene inserted therein.

In step (a), a DNA fragment derived from an attenuated MDV is ligated to a replicable vector to form a first replication vector. The DNA fragment is obtained by cleavage of a genomic DNA of an attenuated MDV with a restriction enzyme as follows.

First, a whole genomic DNA of an attenuated MDV is obtained. Illustratively stated, an attenuated MDV is cultured in a host cell culture such as an avian cell culture according to a customary method, and viral particles are isolated from the host cell culture. For example, a seed attenuated MDV is inoculated to a cell culture of an embryofibroblast derived from a chicken or a quail, and cultured to obtain virus-infected cells. The virus-infected cells are subjected successively to cell lysis; low speed centrifugation to remove cell debris; ultra-centrifugation to extract virus particles; density-gradient centrifugation to isolate and purify the virus particles; and drying. Thus, there are obtained dry virus particles. The genomic DNA of the virus is contained in the virus particle. Therefore, the genomic DNA is isolated from the virus particles and purified according to a customary method as mentioned below. In this instance, for avoiding the irreversible denaturing of a DNA, it is preferred to conduct the isolation and purification at pH 3 to 10. In practicing isolation and purification of the genomic DNA, there may be used customary methods, for example, a hot salt method using a NaCl solution at 100° C., a detergent method using sodium dodecyl sulfate (hereinafter referred to as "SDS"), sodium deoxychlolate (hereinafter referred to as "SDC") or the like, a phenol extraction method, a guanidine hydrochloride method using a concentrated guanidine hydrochloride solution, an alkali method using an NaOH solution, an $Na_2CO_3$—$NaHCO_3$ buffer or the like at about pH 10, and an alcohol precipitation method using cold ethanol. These methods may be used either alone or in combination.

As the attenuated MDV, any of the strains mentioned before may be used.

Second, a DNA fragment is obtained from the genomic DNA. Any DNA fragment from the genomic DNA can be used as long as the DNA fragment contains a portion downstream of a promoter of the genomic DNA. It is more preferred that the DNA fragment also contain a promoter of the genomic DNA. For determining the desired portion to be contained in the DNA fragment, a restriction map of the genomic DNA is prepared as follows. First, a gene library of the genomic DNA of an attenuated MDV is prepared according to a customary method using various restriction enzymes and a known host-vector system as described in, for example, ATCC Catalogue of Bacteria-Phages-rDNA Vectors, 16th edition, pp. 240–255, published by American Type Culture Collection in 1985. Representative examples of vectors include plasmids pGS3, pMV, pPB101 and the like. Representative examples of hosts include avian cells and mammalian cells. Illustratively stated, the genomic DNA of an attenuated MDV is digested with a restriction enzyme to obtain viral DNA fragments. Using a DNA ligase, the DNA fragments are individually inserted in plasmids at their portions cleaved by a restriction enzyme, to form recombinant plasmids. The recombinant plasmids are individually transferred into host cells to form transformants. By culturing the resultant transformants individually, each of the above-mentioned DNA fragments is cloned to thereby obtain an MDV gene library. From each of the transformants of the gene library, a recombinant plasmid is isolated by a customary method and treated with a restriction enzyme to separate the recombinant plasmid into the plasmid and the viral DNA fragment. The vital DNA fragment is recovered and subjected to agarose gel electrophoresis to determine the molecular weight of each DNA fragment. Based on the molecular weight of each DNA fragment, the transformants of the gene library are classified into groups. From each of the groups, a representative transformant clone is selected, and from each of the selected clones, a recombinant plasmid is isolated. The recombinant plasmid is then digested with a restriction enzyme, and the resultant digests are subjected to low-melting point agarose gel electrophoresis to isolate the viral DNA fragment. The vital DNA fragment is purified by, for example, phenol extraction and ethanol precipitation. The purified DNA fragment is labeled with a radioisotope by nick translation. Using the labeled DNA fragment as a probe, the transformant clones of the gene library are subjected to colony hybridization, and positive colonies are selected and isolated. From each of the isolated colonies, plasmids are individually isolated. Each plasmid is treated with various restriction enzymes and subjected to agarose gel electrophoresis. Using the resultant agarose gel and the above-obtained probe, Southern hybridization is conducted. Based on the results of the hybridization and the types of restriction enzymes employed, a restriction map of the genomic DNA of the attenuated MDV is prepared. Then, the nucleotide sequence of the genomic DNA is determined by a customary method, for example, the Maxam-Gilbert method and the dideoxy chain termination method [Proceedings of the National Academy of Science, U.S.A., 74, 5463–5467, (1977); and Analytical Biochemistry, 152, 232–238, (1986)]. Based on the restriction map and nucleotide sequence of the genomic DNA of the attenuated MDV, a portion to be cut off from the genomic DNA and used as a DNA fragment to be ligated to a replicable vector is determined. For secure expression of a foreign gene when the foreign gene is inserted in the genomic DNA of an attenuated DNA, it is preferred that the DNA fragment contain a promoter of the genomic DNA of the attenuated MDV. More preferred is the use of a promoter having an excellent power of gene expression, for example, a promoter of gA antigen gene, a promoter of gB antigen gene, an antigen C gene, a gene coding for a DNA-binding protein having a molecular weight of about 135,000, genes coding for major virus-specific proteins respectively having molecular weights of about 86,000 and about 92,000, and genes coding for phosphorylated proteins respectively having molecular weights of about 36,000, about 39,000 and about 44,000. The cutting-off of a DNA fragment containing a desired portion from the genomic DNA of an attenuated Marek's virus may be conducted according to a customary method using an appropriate restriction enzyme. Alternatively, a DNA fragment containing a desired portion may also be obtained from the above-mentioned gene library as follows. That is, a transformant which contains a recombinant plasmid comprising a desired DNA fragment is selected from the gene library, and cultured. From the cultured transformant, the recombinant plasmid is extracted and digested with an appropriate restriction enzyme. The resultant digests are subjected to low-melting point agarose gel electrophoresis in the same manner as mentioned above to collect the desired DNA fragment.

The thus obtained DNA fragment is ligated to a commercially available replicable vector according to a customary method using a DNA ligase, to form a first replication vector. With respect to a replicable vector, it is necessary to use a replicable vector which is capable of being transfected into a host cell for an attenuated Marek's disease virus, such as as avian cell. Examples of replicable vectors are listed in the ATCC Catalogue of Bacteria-Phages-rDNA Vectors, 16th edition, pp. 240–255, published by the American Type Culture Collection (1985). As the replicable vectors, there can be employed the same vectors as mentioned in connection with the preparation of the gene library of the genomic DNA of an attenuated MDV, such as plasmids pGS3, pMV and pPB101.

The thus obtained first replication vector is introduced in a host cell to form a transformant. The transformant is cultured to multiply the replication vector. From the cultured transformant, the replication vector is extracted in the same manner as mentioned above. Then, the extracted replication vector is co-precipitated with an inorganic salt, such as calcium phosphate. With the resultant precipitate, a higher animal cell such as a mammalian cell or an avian cell is transfected. The resultant cell is cultured and subjected to examination by, for example, an immunocytochemical method, such as an immunofluorescence method using a commercially available fluorescent antibody as a secondary antibody, or a colony hybridization, so as to confirm whether the first replication vector contains a desired DNA fragment.

In step (b), at least one foreign gene sequence derived from another source is inserted in the DNA fragment of the above-obtained first replication vector to form a second replication vector. As the foreign gene, any foreign genes mentioned before may be used. For expressing the foreign gene, it is necessary to insert the foreign gene in the DNA fragment at such a portion that after homologous recombination between the DNA fragment containing the foreign gene and a portion of the genomic DNA of the attenuated Marek's disease virus, which will be mentioned later, the foreign gene is inserted in the genomic DNA in a correct reading frame downstream of at least one promoter of the genomic DNA, which promoter is functional in a host cell for expressing the foreign gene.

The foreign gene used for inserting in the first replication vector may be prepared from a genome exogenous to the attenuated MDV in substantially the same manner as in the case of the preparation of the DNA fragment of the genomic DNA of the attenuated MDV as mentioned above. When the exogenous genome is comprised of RNA, it is necessary to prepare a DNA complementary to the genome by a customary method using a commercially available reverse transcriptase. For the proper insertion of the foreign gene in the first replication vector, it is preferred to prepare the restriction map of the foreign gene and determine the nucleotide sequence of the foreign gene. The preparation of the restriction map and determination of the nucleotide sequence can be conducted in the same manner as mentioned above.

The insertion of the foreign gene in the first replication vector may be conducted by a customary method. Illustratively stated, the first replication vector is cleaved by an appropriate restriction enzyme and the foreign gene is ligated to the cleaved site of the first replication vector by means of a DNA ligase to form a second replication vector. With the resultant vector, a host cell is transformed. The resultant transformant is cultured to multiply the second replication vector. When, for example, the first replication vector contains a DNA fragment comprising a structural gene of the attenuated MDV and its promoter, the foreign gene can be inserted in the DNA fragment at its portion downstream of the promoter and upstream of the initiation codon of the structural gene so that the polypeptide encoded by the foreign gene may be produced by gene expression separately from the protein encoded by the structural gene. Alternatively, the foreign gene can also be inserted in the DNA fragment at its portion within the structural gene so that a fused protein of the polypeptide encoded by the foreign gene and the protein encoded by the structural gene may be produced.

In step (c), a cell is cotransfected with the second replication vector obtained above and with an attenuated Marek's disease virus (MDV).

As the attenuated MDV used for the cotransfection, there may be used the same strain as that used for obtaining the DNA fragment of the first replication vector. Alternatively, there may also be used a strain which is different from the strain used for obtaining the DNA fragment.

As the cell to be cotransfected with the second replication vector and the attenuated MDV, any cell can be used as long as an attenuated MDV can be proliferated in the cell. However, since the MDV has a high infectivity to an avian cell, it is preferred to use, as a host cell, a cell derived from a healthy bird or a specific-pathogen-free (SPF) bird. For example, the use of a primary cell culture or the 2nd to about 5th subculture obtained by serial passage thereof, of an embryofibroblast or embryokidney cell derived from an SPF chicken, an embryofibroblast of a turkey, an embryofibroblast of a quail or the like is preferred.

The cotransfection may be conducted according to a customary method. For example, an attenuated MDV and the coprecipitate of the second replication vector with an inorganic salt obtained in a manner as mentioned above in step (b) are successively inoculated to the culture of a host cell to cotransfect the cell with the attenuated MDV and the second replication vector.

In step (d), the cotransfected cell is incubated for a time sufficient for homologous recombination to occur between the DNA fragment of the second replication vector containing the DNA fragment of Marek's disease virus genome together with the foreign gene, and a portion of the genomic DNA of the attenuated MDV having a homologous or similar nucleotide sequence to the DNA fragment.

The incubation of the cotransfected cell may generally be conducted in a commercially available maintenance medium contained in a container for cell culture at about 30° to about 39° C. for about 15 to about 30 hours.

In step (e), a recombinant virus comprising an attenuated MDV and a foreign gene inserted therein is isolated from the cultured cell as follows.

After the incubation of the cotransfected cells in step (d), the maintenance medium is discarded. The cells are adhering to the inner surface of the container. Then, a fresh maintenance medium containing agarose is overlaid on the cells, followed by incubation at about 30° to about 39° C. for about 1 to 3 days, to form plaques. Each plaque is collected together with a portion of agarose gel using, for example, a cork borer, and transferred onto a commercially available membrane filter in a manner like stamping. The filter is subjected to denaturing, neutralization, etc. to immobilize each stamped plaque on the filter and bake the immobilized plaque. The resultant filter is subjected to plaque hybridization according to a customary method using as a probe a replica of the foreign gene labeled with a radioisotope by nick translation. The stamped plaque which hybridizes with the probe is regarded as positive. The recombinant virus is extracted from the agarose gel containing a plaque which corresponds to the positive plaque stamped on the filter.

Whether the thus obtained recombinant virus is capable of expressing not only the Marek's disease virus antigen genes but also the foreign gene can be examined by, for example, an enzyme-linked immunosorbent assay (ELISA), a fluorescent antibody technique and the like. Further, whether the recombinant virus can be used effectively and safely as a live vaccine can be examined by various customary methods, for example, immunoassay, virological examination method, genetic examination method, histopathological examination method and the like. Such examination methods are described in, for example, Standards for Veterinary Biologics (Notification No. 599 of the Ministry of Agriculture, Forestry and Fisheries, Japan).

The thus obtained recombinant virus may generally be multiplied on a large scale by transfecting into the above-mentioned host cell and culturing the host cell at about 33° to about 39° C. in a customarily employed or commercially available medium for cell culture, such as M199 medium (manufactured and sold by Difco Laboratories, U.S.A.) and Eagle's MEM (manufactured and sold by Nissui Pharmaceutical, Co., Ltd., Japan). As the method of culturing the host cell, any method of static culture, rotary shaking culture, tank culture and the like may be used.

The recombinant virus of the present invention may be used as an active ingredient for a multifunctional Marek's disease live vaccine. Therefore, according to the present invention, there is provided a multifunctional Marek's disease live vaccine comprising:

an immunogenically effective amount of a recombinant Marek's disease virus comprising the genomic DNA of an attenuated Marek's disease virus and at least one foreign gene derived from another source, wherein the foreign gene is inserted in the genomic DNA in a correct reading frame downstream of at least one promoter of the genomic DNA, which promoter is functional in a host cell for expressing the foreign gene, said recombinant Marek's disease virus having an antigenicity and immunogenicity of a Marek's disease virus and containing a polypeptide encoded by the foreign gene; and at least one pharmaceutically acceptable carrier, diluent or excipient.

The term "multifunctional" used herein means "having a function ascribed to a polypeptide encoded by the foreign gene in addition to the antigenicity and immunogenicity of the attenuated MDV". For example, when the foreign gene codes for an antigen of a Marek's disease virus strain different from the attenuated MDV in which the foreign gene is inserted, the multifunctional live vaccine of the present invention acts as a polyvalent vaccine. When the foreign gene codes for an antigen of a virus which is of a species different from the attenuated MDV, the multifunctional live vaccine of the present invention acts like a conventional mixed vaccine. Further, when the foreign gene codes for a structural protein having an adjuvant effect for the immunogenicity of a vaccine, the multifunctional vaccine of the present invention acts as an adjuvant vaccine. The multifunctional Marek's disease live vaccine of the present invention may be supplied in such a form as is contained and sealed in a container such as a vial and an ampoule. As a pharmaceutically acceptable carrier, diluent or excipient, a sterilized isotonic solution such as a physiological saline and a phosphate buffer may be added to the recombinant virus. The resultant vaccine is in the form of a suspension. In this case, it is preferred that a peptone, amino acid, saccharide or the like be incorporated as a stabilizer in the suspension. Alternatively, the recombinant virus contained in a container may also be in the lyophilized form.

According to the present invention, there is further provided a method for producing a multifunctional Marek's disease live vaccine which comprises:

(1) culturing a recombinant Marek's disease virus in an avian cell culture, which recombinant Marek's disease virus comprises the genomic DNA of an attenuated Marek's disease virus and at least one foreign gene derived from another source, wherein the foreign gene is inserted in the genomic DNA in a correct reading frame downstream of at least one promoter of the genomic DNA, which promoter is functional in a host cell for expressing the foreign gene, said recombinant Marek's disease virus having an antigenicity and immunogenicity of a Marek's disease virus and containing a polypeptide encoded by the foreign gene;

(2) isolating the multiplied recombinant Marek's disease virus from the avian cell culture; and (3) adding to the resultant recombinant Marek's disease virus at least one pharmaceutically acceptable carrier, diluent or excipient.

The culturing of the recombinant Marek's disease virus of the present invention in an avian cell culture may be conducted in the same manner as mentioned before. Further, the isolation of the multiplied recombinant Marek's disease virus from the avian cell culture may be conducted in the same manner as mentioned before. To the thus isolated recombinant virus is added at least one of the above-mentioned pharmaceutically acceptable carrier, diluent or excipient. The thus obtained vaccine is in the form of a suspension. If desired, the suspension may be subjected to lyophilization to obtain a lyophilized vaccine.

Generally, a vaccine is administered in the form of a suspension. Therefore, when the recombinant virus of the present invention is in the lyophilized form, the recombinant virus of the present invention is suspended in the above-mentioned sterilized isotonic solution before administration. The concentration of the present recombinant virus in the vaccine for administration may generally be about 10 to 10,000 plaque-forming unit (PFU)/ml. Generally, the vaccine may be administered subcutaneously or intramuscularly. The dose of the vaccine per adult may generally be in the range of from 0.1 to 5.0 ml. The vaccine may generally be administered twice at an interval of about one week to one month and then, about one year later, administered once more.

Further, the recombinant virus of the present invention may be used as an immunological diagnostic for detecting infection with any of Marek's disease virus and the virus from which the inserted foreign gene is derived. For example, the recombinant virus of the present substance is useful for use in ELISA, hemagglutination test, passive hemagglutination test, complement fixation test and other various tests in which a recombinant virus labeled with a fluorescent pigment, an enzyme, a radioisotope, etc. are respectively used.

The recombinant virus of the present invention has the following advantages.

(1) When a gene coding for an antigen, which gene is derived from a virus different in strain or species from the attenuated MDV strain used as a virus vector, is used as a foreign gene to be inserted in the genomic DNA of the attenuated MDV, the resultant virus has not only the antigenicity and immunogenicity of the attenuated MDV strain, but also those of the different type of a virus strain or species. Therefore, the recombinant virus as such can advantageously be used as an active ingredient for a multifunctional vaccine.

(2) As the attenuated MDV used as a virus vector in the present invention, nonpathogenic attenuated strain which is genetically stable is used. Therefore, the recombinant virus of the present invention is extremely stable and free from the danger of reverse mutation to a pathogenic and virulent virus. Accordingly, the safety of the present recombinant virus as a live vaccine can be secured.

(3) A foreign gene is inserted in the genomic DNA of an attenuated MDV in a correct reading frame downstream of a promoter of the genomic DNA. Therefore, the foreign gene can be effectively expressed without adversely affecting the expression of the genes of the attenuated MDV.

(4) According to the present invention, a exogenous promoter is not used, but a promoter of an attenuated MDV is used. Therefore, the promoter used for expressing the foreign gene is completely compatible with a host cell which is used for multiplying the recombinant virus, or a subject which is inoculated with the present recombinant virus as a live vaccine. Particularly, since the most compatible host of the recombinant virus of the present invention is an avian cell or body, if the foreign gene is derived from a virus infectious to an avian cell, the compatibility of the recombinant virus with a host becomes highest, enabling the genes of the recombinant virus of the present invention to be expressed most effectively.

(5) Further, as a promoter of the genomic DNA of the attenuated MDV, downstream of which a foreign gene is inserted, a promoter having a strong power of expression of a gene is utilized in the present invention. Therefore, the expression of the foreign gene inserted in the genomic DNA of an attenuated MDV is performed effectively as well as the expression of the genes of the attenuated MDV.

(6) Further, a host cell suitable for multiplying the present recombinant is a primary culture of an avian cell or a subculture thereof, which can be obtained easily at low cost. Therefore, the recombinant virus of the present invention can be multiplied on a large scale at low cost, leading to an increase in productivity of the desired multifunctional live vaccine.

(7) Further, such a host cell has substantially no danger that the cell is contaminated with a harmful substance, such as a carcinogenic substance. Therefore, according to the present invention, a safe live vaccine can be produced.

(8) Furthermore, as mentioned above, the recombinant virus of the present invention as such can be used as an active ingredient for a multifunctional live vaccine. This means that a polyvalent or multifunctional live vaccine can be obtained by a method in which only the recombinant virus of the present invention is cultured, which is simple and easy as compared to a conventional method for producing a polyvalent or multifunctional live vaccine, in which a plurality of types of strains or species of viruses must be cultured separately and then mixed together.

The present invention will now be described in more detail with reference to the following Reference Examples and Examples which should not be construed as limiting the scope of the present invention.

REFERENCE EXAMPLE 1

Preparation of a Phosphate Buffer Solution:

A phosphate buffer solution (hereinafter referred to as "PBS") was prepared by mixing a base solution I containing 8.0 g/l of NaCl, 0.2 g/l of KCl and $\frac{1}{15}$M Na$_2$HPO$_4$ with a base solution II containing 8.0 g/l of NaCl, 0.2 g/l of KCl and $\frac{1}{15}$M KH$_2$PO$_4$ in a volume ratio such that the resultant mixture had a predetermined pH to be employed in respective Example.

REFERENCE EXAMPLE 2

Preparation of a Trypsin Solution:

2.5 g of trypsin 1:250 (manufactured and sold by DIFCO Co., U.S.A.) was dissolved in the $\frac{1}{15}$M PBS (pH 7.2) prepared in the manner as described in Reference Example 1 so that the total volume of the resultant solution became 1 l. The resultant solution was sterilized by filtration by means of a membrane filter, to thereby obtain a trypsin solution.

REFERENCE EXAMPLE 3

Preparation of a Tris Buffer Solution:

121.14 g of tris(hydroxymethyl)aminomethane (hereinafter referred to as "Tris") was dissolved in 800 ml of distilled water, and to the resultant solution was dropwise added concentrated HCl so that the pH value of the resultant solution was adjusted to a predetermined degree to be employed in respective Example. Then, distilled water was added to the solution in such an amount that the total volume of the resultant solution became 1 l, thereby obtaining a 1M Tris buffer solution. The thus obtained solution was diluted with distilled water so as to adjust the concentration of Tris appropriately for use in Examples. The Tris buffer solution is hereinafter referred to as "Tris-HCl".

REFERENCE EXAMPLE 4

Culturing of HVT O1 Strain:

The HVT O1 strain was cultured in accordance with a customary method as follows. Quail embryofibroblasts (hereinafter referred to as "QEF") taken from 7 quail eggs which had been incubated for 9 days was digested with the trypsin solution prepared in Reference Example 2, to thereby obtain an embryofibroblast suspension. The thus obtained suspension was subjected to low-speed centrifugation at 1,000 rpm for 5 minutes to collect the QEF. The collected QEF was suspended in a maintenance medium, i.e., Eagle's MEM (manufactured and sold by Nissui Pharmaceutical Co., Ltd., Japan) containing 5 v/v% of a calf serum so that the final volume and final a cell concentration became 500 ml and 2×10$^6$ cells/ml, respectively. The thus prepared QEF suspension was poured into 5 Roux bottles each having a capacity of 1 l in an amount of 100 ml per bottle. Then, 1 ml of an HVT O1 strain-infected cell suspension having a virus infection degree of 1.0×10$^6$ PFU (plaque-forming unit)/ml was inoculated as a seed virus to each of the bottles. The bottles were closed with a rubber stopper and incubated in an incubator at 37° C. for 2 days. The incubation was terminated after it was confirmed by means of a microscope that the degree of the cytopathic effect, i.e., the ratio of the giant cells to the cells forming a monolayer in each Roux bottle reached 90%. Then, the culture medium was taken out from each of the Roux bottles and 100 ml of $\frac{1}{15}$M PBS (pH 7.4) was poured into each bottle and each bottle was gently shaken to wash the infected cells which form a monolayer covering over the inner wall of each bottle. This washing operation was performed three times. Then, 20 ml of $\frac{1}{15}$M PBS (pH 7.4) was poured into each bottle and, then, pipetting was performed, thereby allowing the infected cells to peel off from the inner wall of each bottle and suspend in the PBS. The resultant infected cell suspensions in the bottles were pooled and subjected to low-speed centrifugation at 2,000 rpm for 10 minutes. The resultant supernatant was removed and the sediment was collected. The thus obtained sediment (about 1 ml) was preserved in a refrigerator at −70° C. for later use as a raw material for preparing HVT genomic DNA.

REFERENCE EXAMPLE 5

Culturing of MDV C2 Strain:

Substantially the same procedure as in Reference Example 4 was performed except that MDV C2 strain was employed instead of HVT O1 strain, thereby obtaining a sediment of MDV-infected QEF cells. The thus obtained sediment of MDV-infected QEF cells was preserved in a refrigerator for later use for the preparation of MDV genomic DNA.

EXAMPLE 1

Step 1

Preparation of HVT Genomic DNA:

To the HVT-infected QEF cells obtained in Reference Example 4 was added 20 ml of TEN$^{50}$ solution (10 mM Tris-HCl (pH 7.4), 1 mM disodium ethylenediamine tetraacetate (hereinafter referred to as "Na$_2$-EDTA") and 50 mM NaCl ), followed by stirring using a stirrer for 5 minutes. Then, to the thus obtained suspension were added 20 ml of a 2×cell lysis solution [100 mM Tris-HClHCl (pH 7.4), 7.2 mM CaCl$_2$, 250 mM KCl, 1 mM Na$_2$-EDTA, 1 w/v % sodium deoxycholate and 1 w/v % Nonidet P-40

(manufactured and sold by Sigma Chemical Company, U.S.A.)], 500 μg of DNase I (manufactured and sold by Takara Shuzo Co., Ltd., Japan) and 1 mg of RNase A (manufactured and sold by Sigma Chemical Company, U.S.A.). The resultant mixture was incubated at 37° C. for 30 minutes to allow a reaction to proceed. Then, 20 ml of trichlorofluoroethane was added to the reaction mixture, followed by vigorous shaking. Then, the mixture was subjected to centrifugation at 4° C. and 1500 rpm for 10 minutes. The resultant supernatant was collected and overlaid on a density-gradient of 5 to 40 w/w % glycerol and subjected to ultracentrifugation at 27,000 rpm at 4° C. using an ultracentrifuge (Model 55P; rotor No. RPS-28, manufactured and sold by Hitachi, Ltd., Japan) to precipitate a nucleocapsid. The supernatant was carefully removed by means of a Pasteur pipette. Thereafter, to the precipitated nucleocapsid was added 200 μl of a 1×cell lysis solution (50 mM Tris-HCl (pH 7.4), 3.6M $CaCl_2$, 125 mM KCl, 0.5 mM $Na_2$-EDTA, 0.5% sodium deoxycholate and 0.5 w/v % Nonidet P-40), and the resultant mixture was stirred at 0° C. for 5 minutes by means of a stirrer. The resultant suspension was put into an Eppendorf tube (manufactured and sold by Eppendorf-Netheler-Hinz GmbH, West Germany), and into the Eppendorf tube were further added 200 μl of a solution of 10 mg/ml proteinase K (manufactured and sold by Sigma Chemical Company, U.S.A.) and 600 μl of 2×STE solution (100 mM Tris-HCl (pH 7.4), 20 mM $Na_2$-EDTA and 2 w/v % sodium dodecyl sulfate). The resultant mixture was kept at 65° C. for 30 minutes to allow a reaction to proceed. Thereafter, the reaction mixture was subjected to phenol extraction with an equivolume of water-saturated phenol and then 2 times with a mixed organic solvent (phenol:chloroform:isoamylalcohol=25:24:1, volume ratio). The aqueous phases were collected and a double volume of cold ethanol was added to the aqueous phase and the resultant mixture was allowed to stand still at −20° C. overnight to precipitate DNA. The mixture was subjected to centrifugation to collect the DNA and the DNA was dried. The dried DNA was suspended in 500 μl of TE solution [10 mM Tris-HCl (pH 8.0) and 1 mM $Na_2$-EDTA] to thereby obtain an HVT genomic DNA suspension.

Step 2

Cloning of Restriction Enzyme-cleaved Fragments of the HVT Genomic DNA and Preparation of a Gene Library:

In this step, the HVT genomic DNA obtained in Step 1 was digested with each of the three types of restriction enzymes, i.e., BamHI, HindIII and PstI, and the resultant DNA fragments were cloned, using cosmid pHC79 (manufactured and sold by BRL Inc., U.S.A.), as follows.

1 μg of the HVT genomic DNA obtained in Step 1 was digested in 10 μl of a 1×RM solution [50 mM Tris-HCl (pH 7.4), 10 mM $MgCl_2$, 1 mM dithiothreitol (hereinafter referred to as "DTT") and 100 mM NaCl] containing 10 units of restriction enzyme BamHI (manufactured and sold by Nippon Gene Co., Japan). Separately, 100 mg of pHC79 was completely digested with BamHI in 50 μl of a solution having the same composition as mentioned just above. With respect to each of the resultant reaction mixtures, phenol extraction and ethanol precipitation were performed in the same manner as described above, to thereby obtain the HVT genomic DNA fragments and the cosmid fragment. The thus obtained HVT genomic DNA fragments and the cosmid fragment were mixed with each other in such a proportion that the weight ratio of the HVT genomic DNA fragments to the cosmid fragment became 10:1, and the resultant mixture was kept at 20° C. for 2 hours in 10 μl of a solution containing 60 mM Tris-HCl (pH 7.6), 6.6 mM $MgCl_2$, 10 mM DTT, 1 mM ATP and 100 units of T4 DNA ligase (manufactured and sold by Takara Shuzo Co., Ltd., Japan) to ligate the HVT genomic DNA fragments individually with the cosmid pHC79 fragment at its BamHI site, thereby obtaining a recombinant plasmid.

The above-obtained recombinant plasmid was transferred into a recipient cell *E. coli* DH5 strain (manufactured and sold by BRL Inc., U.S.A.) as follows.

*E. coli* DH5 strain was cultured by shake culturing at 30° C. overnight in 10 ml of S medium (0.5 w/v % bactoyeast extract, 2 w/v % bactotrypton and 0.5 w/v % magnesium sulfate). Thereafter, 1 ml of the resultant culture was taken and diluted 100 times with the S medium and subjected to shake culturing at 30° C. until the optical density at 550 nm ($OD_{550}$) of the culture became 0.48. Subsequently, the culture was cooled in ice water for 10 minutes and then subjected to centrifugation at 5,000 rpm for 10 minutes, to harvest the cultured cells. 10 ml of a transformation solution I (30 mM potassium acetate, 100 mM RbCl, 10 mM $CaCl_2$ and 15 w/v % glycerol) was added to the above-obtained cells to obtain a cell suspension. The resultant suspension was cooled in ice water for 10 minutes and then subjected to centrifugation at 5,000 rpm for 10 minutes to collect the cells. The cells were suspended in 1 ml of a transformation solution II [10 mM piperadine-N,N'-bis(2-ethanesulfonic acid) (PIPES) (manufactured and sold by Dojindo Laboratories, Japan), 75 mM $CaCl_2$, 10 mM RbCl and 15 w/v % glycerol] and the resultant suspension was taken into Eppendorf tubes in an amount of 200 μl per tube and kept at −70° C. for preservation.

200 μl of the above-obtained suspension containing the recipient cells was thawed and mixed with 1 μl of the above-obtained recombinant plasmid and the resultant mixture was allowed to stand still at 0° C. for 30 minutes, followed by heat shock treatment at 42° C. for 2 minutes. Subsequently, 800 μl of S medium was added to the mixture and the resultant mixture was allowed to stand still at 30° C. for 60 minutes, followed by centrifugation to harvest the cells. The cells were inoculated on an L agar plate (1 w/v % bactotrypton, 0.5 w/v % NaCl, 0.5 w/v % yeast extract, 1.5 w/v % agar and 25 μg/ml ampicillin) and incubated at 37° C. overnight, to thereby obtain colonies of transformants. Thereafter, each of the colonies of transformants was transferred to both of an L agar plate containing ampicillin at a concentration of 25 μg/ml and an L agar plate containing tetracycline at a concentration of 10 μg/ml, respectively, and the plates were incubated at 37° C. overnight. Since the transformants containing the digested HVT genomic DNA are resistant to ampicillin but sensitive to tetracycline, the colonies of the transformants resistant to ampicillin but sensitive to tetracycline were selected. The thus obtained colonies are designated "BamHI library of HVT genomic DNA".

Substantially the same procedures as described above were repeated except that each of restriction enzymes HindIII and PstI was individually employed instead of BamHI, thereby obtaining HindIII library and PstI library of HVT genomic DNA, respectively, and that in the case of the use of PstI, selection of the desired transformants was performed using, as a criterion, sensitivity to ampicillin and resistance to tetracycline.

Step 3

Figure 1:
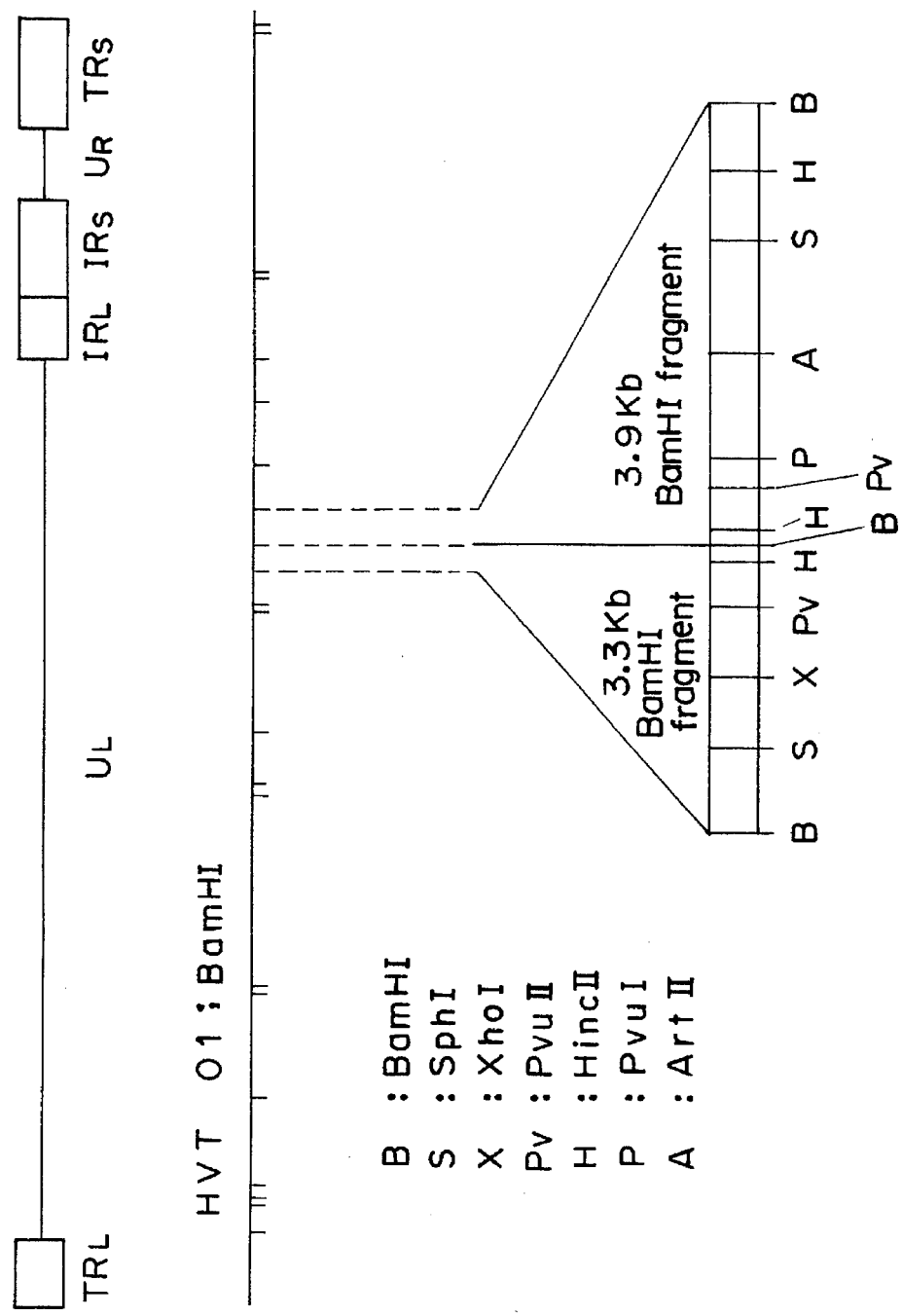
FIG. 1 shows a restriction map of the genomic DNA of HVTO1 strain.
Figure 2:
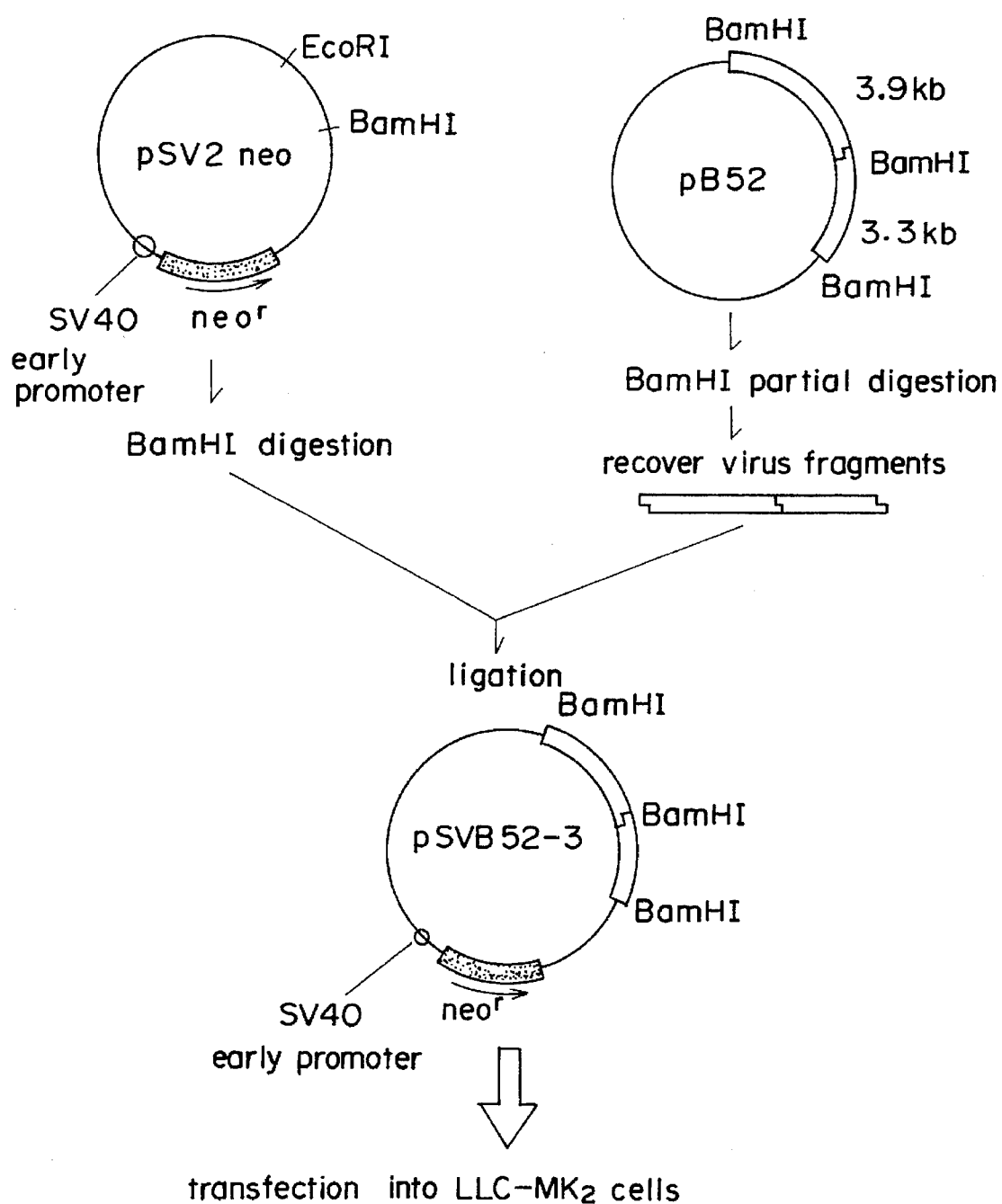
FIG. 2 shows a flow chart indicating the construction of an expression vector pSVB52-3 for expressing the glycoprotein A antigen (hereinafter referred to as "gA antigen") of HVT.

Preparation of a Restriction Map of the Genomic DNA of HVT:

A restriction map of the genomic DNA of HVT was prepared using the techniques of the colony hybridization as described in "Manual for Genetic Engineering", pp. 51–54 (1982), published by Kodansha Scientific, and the Southern blot hybridization as described in "Molecular Cloning", pp. 382–389 (1982), published by Cold Spring Harbor Laboratory. Illustratively stated, plasmid DNA's were individually extracted from each of 1128 clones in the BamHI library obtained in Step 2 by an alkali extraction method described in the above-mentioned "Molecular Cloning" pp. 368–369. Each of the thus extracted plasmid DNA's was completely digested with restriction enzyme BamHI, and subjected to agarose gel electrophoresis to determine the mobility of the digests of the plasmid DNA. From the mobility, the molecular weight of each of the BamHI fragments obtained from the HVT genomic DNA, which were cloned by means of plasmid pHC79, was calculated. Further, the above-obtained plasmid DNA was digested with each of restriction enzymes HindIII and PstI, followed by the same agarose gel electrophoresis as mentioned above to obtain cleavage patterns of the plasmids with respect to each of the restriction enzymes. Based on the results, the clones in the BamHI library were classified into groups so that each group consists of clones having a similar cleavage pattern. From each of the above-classified groups, a typical clone was selected. Then, each of the selected clones was separately digested with BamHI, and subjected to low-melting point agarose gel electrophoresis to collect only cloned DNA fragments of HVT genomic DNA. The thus obtained DNA fragments were purified by phenol extraction and ethanol precipitation in substantially the same manner as described in Step 1. Then, according to the nick translation method as described in the above mentioned textbook "Manual for Genetic Engineering" pp. 83–86, the purified DNA fragments were labeled with [$^{32}$P]-dCTP. Using the thus obtained $^{32}$P-labeled DNA fragments as a probe, colony hybridization was conducted with respect to each of the HindIII library and PstI library obtained in Step 2. From the positive colonies which hybridized with the probe by colony hybridization, a plasmid DNA was isolated according to the alkali extraction method as described above. Then, the thus extracted DNA was digested with various restriction enzymes as indicated in FIG. 1 and subjected to agarose gel electrophoresis. Using the resultant gel, Southern hybridization was conducted. Based on the results of the Southern hybridization, a restriction map of the genomic DNA of HVT was prepared. The results are shown in FIG. 1. In FIG. 1, the upper row diagrammatically illustrates the structure of the genomic DNA of the HVT O1 strain. The abbreviations used in FIG. 1 have the following meanings: $TR_L$, long terminal repeat; $TR_S$, short terminal repeat; $IR_L$, long internal repeat; $IR_S$, short internal repeat; and $U_L$, long unique region.

Step 4

Construction of an Expression Vector for Expressing the HVT gA Antigen (a First Replication Vector):

A plasmid which was confirmed from the results of the analysis in Step 3 to have two BamHI fragments of the HVT genomic DNA of 3.9 kb and 3.3 kb was designated "pB52". This plasmid was partially digested with BamHI and subjected to agarose gel electrophoresis, to thereby collect a BamHI fragment of 7.2 kb. Then, the thus obtained BamHI fragment was inserted in the BamHI site of plasmid pSV2-neo (ATCC 37149). The thus obtained recombinant plasmid was transferred into a cell of *E. coli* DH5 strain to form a transformant. The plasmid contained in the transformant was designated "pSVB52-3". The above-mentioned procedure is illustrated in FIG. 2. Further, the plasmid pSVB52-3 was extracted from the transformant by the alkali extraction method as described in Step 3 and dried.

Step 5

Transfection of Plasmid pSVB52-3 into a Mammalian Cell and Detection of the HTV gA Antigen:

5 μg of plasmid pSVB52-3 was dissolved in 200 μl of 2×HBS [50 mM N-2-hydroxyethylpiperazine-N'-2-ethanesulfonic acid (HEPES) (manufactured and sold by DOJINDO Laboratories, Japan), 280 mM NaCl and 1.5 mM $Na_2HPO_4$]. To the resultant solution was added 200 μl of 0.25M aqueous $CaCl_2$ solution. Then, the resultant mixture was incubated at 20 ° C. for 30 min, thereby forming a co-precipitate of the plasmid DNA with calcium phosphate. On the other hand, a simian kidney cell LLC-$MK_2$ (ATCC CCL 7) was cultured for 24 hours in a petri dish having a diameter of 6 cm. To the resultant culture was dropwise added the above-obtained mixture containing the co-precipitate by means of a micropipette. Then, the resultant cell culture was incubated in a $CO_2$ incubator for 20 hours. To the resultant cell culture was added the trypsin solution prepared in such Reference Example 2 to peel the cells off from the surface of the petri dish. Then, the culture was subjected to centrifugation by the method as described in Reference Example 3 to collect cells. The thus collected cells were subcultured using an Eagle's MEM medium (manufactured and sold by Nissui Pharmaceutical Co., Ltd., Japan) containing 400 μg/ml of G418 (manufactured and sold by Sigma Chemical Company, U.S.A.) and 5% (v/v) of fetal calf serum. A mammalian cell transformed with plasmid pSVB52-3 had to be resistant to an antibiotic aminoglycoside G418. Therefore, the colonies of the transformants were selected using, as a criterion, the resistance to G418. Then, the selected colonies were subjected to subculturing for 10 days. Then, the subcultured cells of each colony were cloned using a trypsin solution-infiltrated filter and the resultant nclone were cultured individually. Then, the culture of each clone was examined to determine whether or not an HVT gA antigen was detected in the culture by a customary avidin-biotin immunofluorescence technique (BRL Products for Immunodetection—Application Guide—, No. 10444, published by Bio-Rad Laboratories, U.S.A.). For the detection, a monoclonal antibody M-34 (Journal of General Virology, Vol. 64, pp. 2597–2610, 1983) which is capable of reacting with both an HVT gA antigen and an MDV gA antigen was used as a primary antibody and an anti-mouse IgG (manufactured and sold by Bio-Rad Laboratories, U.S.A.) was used as a secondary antibody. As a result, it was found that with respect to about one-third of the G418 resistant clones, a fluorescence specific to an HVT gA antigen was detected in the cytoplasm of the cells of each clone. This indicates that an HVT gA antigen was produced by these clones. The photograph of the representative clone which was assayed by the avidin-biotin immunofluorescence technique is shown in FIG. 12.

Step 6

Determination of the Nucleotide Sequence of the gA Antigen Gene of HVT:

Plasmid pSVB52-3 capable of expressing the HVT gA antigen gene obtained in Step 4 was digested with restriction enzyme BamHI and subjected to low-melting point agarose gel electrophoresis, to collect a 7.2 kb BamHI fragment of the HVT genomic DNA. The thus obtained BamHI fragment was further digested with various restriction enzymes. Each of the thus obtained DNA digests was inserted in the BamHI site of plasmid pSV2-neo in the same manner as described in Step 4. Then, the resultant plasmids were individually transfected in LLC-MK$_2$ cells to form transformants, and whether or not an HVT gA antigen was produced in the transformants was examined. As a result, it was found that the region of the HVT gA antigen gene was present in the SphI—SphI region indicated in FIG. 1, and that one of the plasmids had the gA antigen gene of the HVT in its entirety. This plasmid was designated "pSBS-1". Then, from the plasmid pSBS-1, an SphI—SphI fragment corresponding to the above-mentioned SphI—SphI region was cut off in the same manner as mentioned above with respect to the cut-off of the BamHI fragment. Using the resultant SphI—SphI fragment, the whole nucleotide sequence of the gA antigen gene of the HVT was determined by a customary dideoxy chain termination method as described above. The nucleotide sequence of the gA antigen gene of the HVT and the amino acid sequence encoded thereby are shown in FIGS. 3(a) to 3(K), together with the nucleotide sequence of the gA antigen gene of MDV and the amino acid sequence encoded thereby, which will be mentioned later in Example 3. In FIGS. 3(a) to 3(k), the sequences are arranged in the following order from the top row through the bottom row:

(1) nucleotide sequence coding for the gA antigen of MDV;

(2) amino acid sequence of the gA antigen of MDV deduced from the nucleotide sequence (1) mentioned above;

(3) nucleotide sequence coding for the gA antigen of HVT; and (4) amino acid sequence of the gA antigen of HVT deduced from the nucleotide sequence (3) mentioned above.

Step 7

Cloning of the Gene Coding for Hemagglutinin and Neuraminidase (hereinafter referred to as "HN gene") of Newcastle Disease Virus (hereinafter referred to as "NDV"):

In this Example, as a foreign gene, the HN gene of NDV was used. The HN gene was obtained as follows.

According to a cusromary method, 0.5 ml of seed virus solution of NDV FUDAI strain (commercially available from The Japanese Association of Veterinary Biologics, Japan) was inoculated into the allantoic cavity of each of ten 10-day embryonated chicken eggs, and incubated at 37° C. for 2 days. Then, an allantoic fluid was collected from each of the incubated eggs. Thus, there was obtained about 50 ml of allantoic fluid. The allantoic fluid was subjected to centrifugation at 10,000 g for 15 min, and a supernatant was collected. The supernatant was subjected to ultracentrifugation using an ultra-centrifuge Model 55P and a rotor No. PR-21 (manufactured and sold by Hitachi, Ltd., Japan) at 21,000 rpm at 4° C. for 90 min, to thereby collect NDV particles. The thus obtained NDV particles were suspended in 1 ml of a PK buffer (0.1M Tris-HCl (pH 7.4), 12.5 mM Na$_2$-EDTA, 0.15M NaCl and 1 w/v % of sodium dodecyl sulfate). Then, to the resultant suspension was added 100 µl of an aqueous proteinase solution having a proteinase concentration of 4 mg/ml. The mixture was incubated at 65° C. for 30 min. The resultant mixture was subjected to phenol extraction and ethanol precipitation in the same manner as described in Step 1, to thereby obtain a purified genomic RNA of NDV. 5 µg of the thus obtained NDV genomic RNA was added to 100 µl of a solution containing 50 mM Tris-HCl (pH 7.9), 100 mM KCl, 10 mM MgCl$_2$, 10 mM DTT, 1 mM nucleoside triphosphate, 30 units of RNase inhibitor (manufactured and sold by Takara Shuzo Co., Ltd., Japan) and 2 µg of a synthetic oligodeoxynucleotide primer (17mer). The resultant mixture was incubated at 60° C. for 15 min to advance a reaction and, then, the reaction mixture was gradually cooled to 42° C. to conduct an annealing. Then, to the resultant mixture was added 10 µl of a 3,300 units/ml reverse transcriptase solution. The resultant mixture was incubated at 42° C. for 90 min to advance a reaction. After completion of the reaction, to the reaction mixture was added a solution containing 50 mM Tris-HCl (pH 7.2), 10 mM MgSO$_4$, 0.1 mM DTT, 50 µg/ml of bovine serum albumin, 20 units of RNase H (manufactured and sold by Takara Shuzo Co., Ltd., Japan), 0.2 units of E. coli DNA ligase (manufactured and sold by Takara Shuzo Co., Ltd., Japan), 0.15 mM β-nicotinamide adenine dinucleotide and 30 units of DNA polymerase so that the final volume of the resultant mixture became 400 µl. The mixture was incubated at 15° C. for 2 hours to advance a reaction. The reaction mixture was subjected to phenol extraction and ethanol precipitation to form precipitates. The thus obtained precipitates were dissolved in 100 µl of a solution containing 50 mM Tris-HCl (pH 7.6), 10 mM MgCl$_2$, 5 mM DTT, 0.1 mM spermidine, 0.1 mM Na$_2$-EDTA and 1 mM adenosine 5-triphosphate. To the thus obtained solution was added 10 µl of a 1,000 units/ml T4 polynucleotide kinase solution. The resultant mixture was incubated at 37° C. for 30 min to advance a reaction. After completion of the reaction, the reaction mixture was subjected to phenol extraction and ethanol precipitation to form precipitates. Then, the thus obtained precipitates were dissolved in 100 µl of a solution containing 33 mM Tris-acetic acid (pH 7.9), 66 mM potassium acetate, 10 mM magnesium acetate, 0.5 mM DTT, 0.1 mg/ml of bovine serum albumin and 0.5 mM deoxynucleoside triphosphate. To the thus obtained solution was added 10 µl of a 400 units/ml T4 DNA polymerase solution. The resultant mixture was incubated at 37° C. for 15 min to advance a reaction. After completion of the reaction, the reaction mixture was subjected to phenol extraction and ethanol precipitation, to thereby obtain complementary DNA's (cDNA) to the various portions of the genomic RNA of NDV.

Figures 4, 4A:
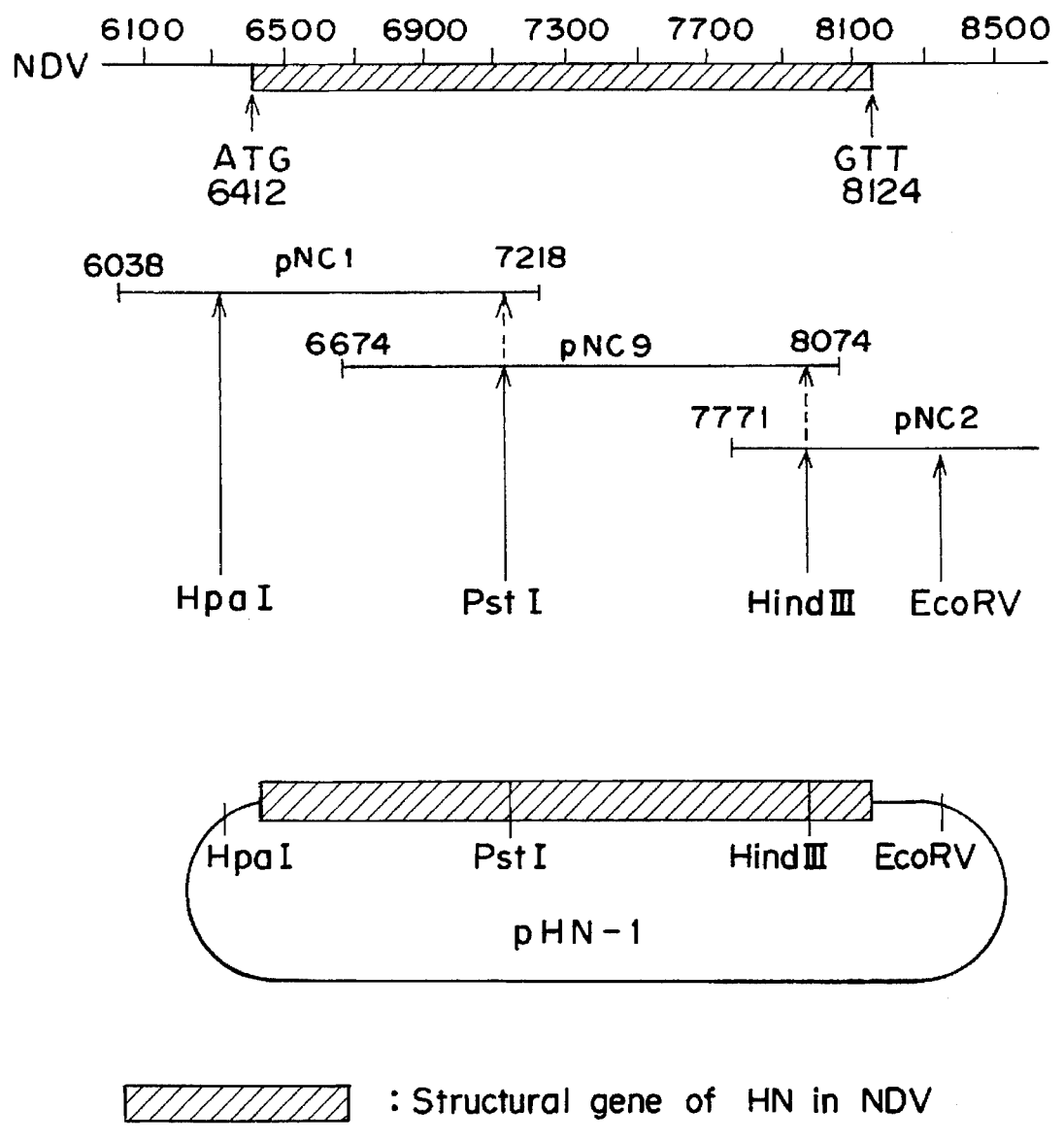

100 ng of the thus obtained cDNA's and 100 ng of plasmid pUC19 (manufactured and sold by Takara Shuzo Co., Ltd., Japan) (Gene, vol. 26, page 101, 1983) which had been cleaved by restriction enzyme HincII were dissolved in 50 µl of a solution containing 60 mM Tris-HCl (pH 7.6), 6.6 mM MgCl$_2$ and 10 mM adenosine 5-triphosphate. Then, to the resultant solution was added 10 µl of a T4 DNA ligase solution having a T4 DNA ligase concentration of 60,000 units/ml. The mixture was incubated at 20° C. for 2 hours to ligate each of the cDNA's to the HincII site of plasmid pUC19 individually. Thereafter, using the resultant mixture, cells of Escherichia coli JM83 (ATCC 35607) were transformed in substantially the same manner as in Step 2. The resultant transformants were cultured to conduct cloning of each of the cDNA fragments of various sizes on the vector plasmid pUC19. From each of the transformants, the recombinant plasmid was isolated, and from the plasmid, the cloned DNA fragment was isolated in substantially the same manner as in Step 3. Then, the nucleotide sequence of each of the cloned DNA fragments was determined in accordance with the dideoxy chain termination method as described in Step 6. As a result, it was found that three cloned cDNA fragments coding for different portions of the HN gene of Newcastle disease virus (NDV) were obtained. The plasmids containing these cloned cDNA fragments were designated "pNC1", "pNC2" and "pNC9", respectively. Then, in order to obtain a cDNA fragment containing the whole HN gene of NDV, the above-cloned cDNA fragments were ligated as follows. First, from the above-obtained plasmids pNC1, pNC2 and pNC9, the cloned cDNA fragments were collected in substantially the same manner as in Step 3. The cDNA fragment obtained from plasmid pNC1 was digested with restriction enzymes HpaI and PstI to obtain a fragment pNC1. The cDNA fragment obtained from plasmid pNC9 was digested with restriction enzymes PstI and HindIII to obtain a fragment pNC9. The cDNA fragment obtained from plasmid pNC2 was digested with restriction enzymes HindIII and EcoRV to obtain a fragment pNC2. Then, the thus obtained fragments were ligated to one another using T4 DNA ligase to obtain a cDNA fragment having the whole HN gene. The thus obtained cDNA fragment was ligated to the HincII site of plasmid pUC19. With the resultant recombinant plasmid, Escherichia coli JM83 was transformed so that the cDNA fragment containing the whole HN gene was cloned. The plasmid carrying the cDNA fragment containing the whole HN gene of NDV was designated "pHN-1". In FIG. 4, the correspondences between the fragments pNC1, pNC2 and pNC9 and the cDNA fragments containing the whole HN gene are illustrated. The cDNA fragment having the whole HN gene of NDV was isolated from the plasmid pHN-1 in substantially the same manner as in Step 3. Then, the nucleotide sequence of the thus obtained cDNA fragment containing the whole HN gene was determined in accordance with the dideoxy chain termination method as mentioned before. The nucleotide sequence of the NH gene and the amino acid sequence deduced therefrom are shown in FIGS. 5(a) to 5(d).

Step 8

Figure 6:
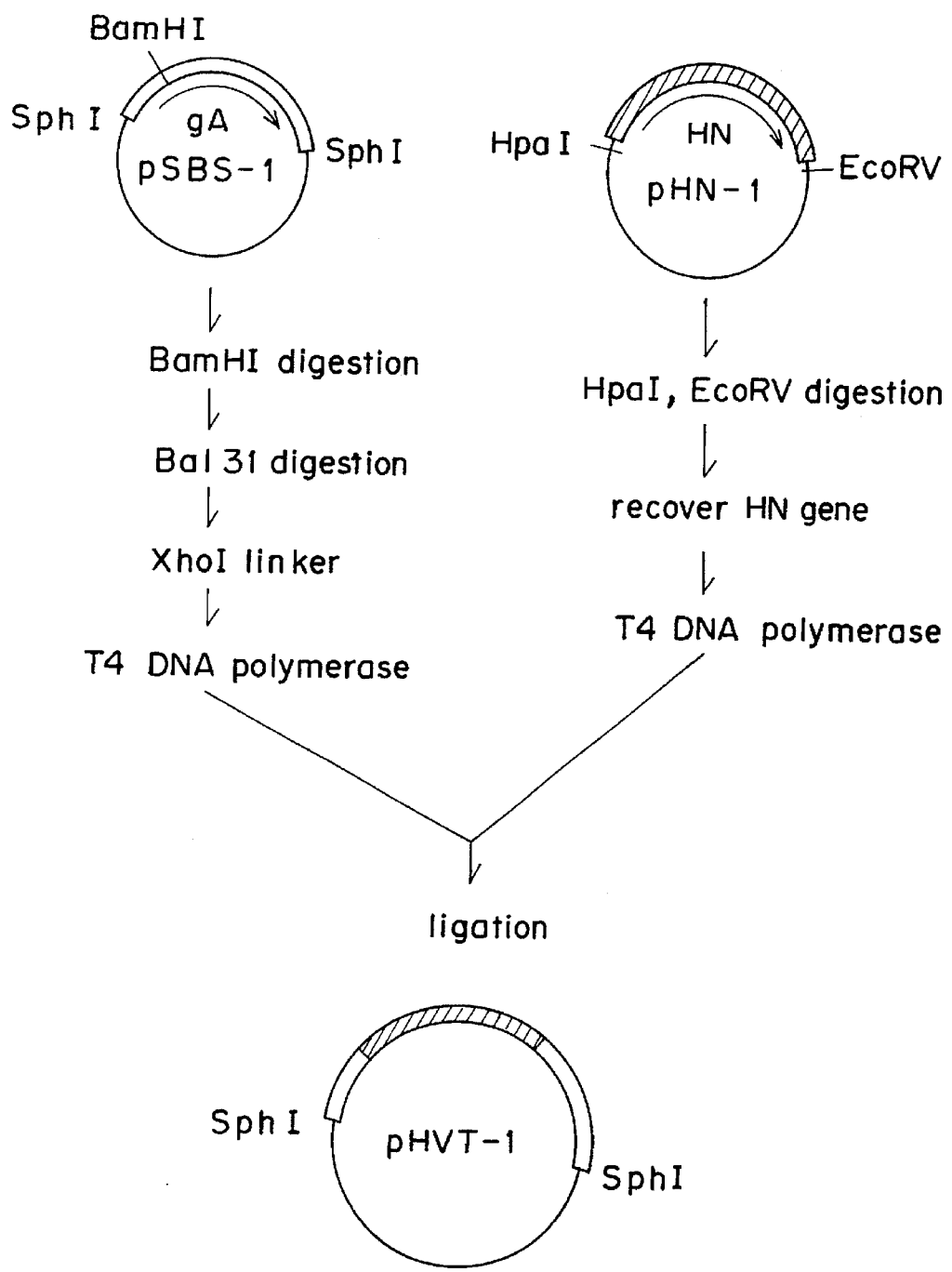
FIG. 6 shows a flow chart indicating the construction of plasmid pHVT-1 comprising the gA antigen gene of HVT and a foreign gene, which plasmid is used for preparing a recombinant virus of the present invention.

Construction of a Second Replication Vector Containing the HVT gA Antigen Gene and a Foreign Gene (HN Gene):

100 ng of plasmid pSBS-1 having the gA antigen gene of HVT which was prepared in Step 6 was cleaved by restriction enzyme BamHI. After the cleavage, the cleaved plasmid was collected by phenol extraction and ethanol precipitation. The collected plasmid was dissolved in 100 µl of a solution containing 50 mM Tris-HCl (pH 7.9), 10 mM $MgCl_2$, 50 mM NaCl, 0.1 mg/ml bovine serum albumin, 1 mM DTT and 1 mM deoxyribonucleoside triphosphate. To the resultant solution was added 10 µl of a T4 DNA polymerase solution having a T4 DNA polymerases concentration of 200 units/ml. The reaction was conducted at 37° C. for 10 minutes to convert both ends of the cleaved plasmid into blunt ends. After completion of the reaction, the resultant reaction mixture was subjected to phenol extraction and ethanol precipitation to recover a plasmid DNA. The plasmid DNA was digested with nuclease Bal31 ("Molecular Cloning" mentioned in Step 3, pages 136–139) to remove the initiation codon ATG of the gA antigen gene of HVT. Then, in accordance with the method described in the above-mentioned Molecular Cloning, pages 243–246, an XhoI linker was ligated to the both ends of the plasmid DNA, and the plasmid DNA was treated with T4 DNA polymerase to convert the both ends of the plasmid DNA into blunt ends. On the other hand, plasmid pHN-1 obtained in Step 6 was digested with restriction enzyme HpaI and EcoRV and subjected to low-melting point agarose gel electrophoresis to recover a DNA fragment of about 1.8 kb containing the HN gene of NDV. Then, the DNA fragment of about 1.8 kb was ligated to the above-obtained plasmid DNA. With the resultant plasmid, a cell of Escherichia coli JM83 strain was transformed to obtain a transformant. The resultant plasmid was designated "pHVT-1". The above procedure is illustrated in FIG. 6.

Step 9

Preparation of a Recombinant HVT:

A QEF cell culture was prepared in a petri dish having a diameter of 6 cm in substantially the same manner as in Reference Example 4. To the QEF cell culture was inoculated $1\times10^6$ PFU/petri dish of seed virus HVT O1 strain. Then, a maintenance medium was added to the culture and the resultant culture was incubated in a carbon dioxide incubator at 37° C. for 2 hours. To the resultant culture was dropwise added a co-precipitate of plasmid pHVT-1 with calcium phosphate, which was obtained in Step 8. Then, the culturing was further conducted for 20 hours. After completion of the culturing, the maintenance medium was gently removed and 6 ml/petri dish of a maintenance medium containing agarose at a concentration of 0.8 w/v % was poured on the cultured cells in the petri dish. The cells were further cultured in a carbon dioxide incubator at 37° C. for 48 hours to form plaques. During the culturing the homologous recombination had occurred between the DNA fragment of plasmid pHVT-1 containing both of the gA antigen gene and the HN gene, and the portion of the genomic DNA of the HVT, which has a homologous or similar nucleotide sequence to the DNA fragment, thereby forming a recombinant HVT. Thereafter, the recombinant HVT was isolated from each of the plaques by the plaque hybridization method as described in Manual for Genetic Engineering, on pages 68–73 (1982), published by Kodansha Scientific, Japan. That is, portions of the agarose gel at which plaques had formed were cut off using a sterilized cork borer having a diameter slightly larger than the diameter of each plaque. The cut-off portions of the agarose gel were pressed against a sterilized nylon membrane filter (manufactured and sold by Nihon Pall Ltd., Japan) in a manner like stamping, to thereby transfer the plaques onto the sterilized nylon membrane filter. The cut-off portions of the agarose gel were stored in a buffer solution containing $\frac{1}{15}$M PBS (pH 7.4), 10 w/v % saccharose, 3 w/v % L-arginine, 1 w/v % gelatin hydrolyzate at −70° C. in a frozen state. The plaque-transferred filter was subjected to customary treatments, i.e., modification with 0.5N NaOH, neutralization with 1M Tris-HCl (pH 7.5) and baking at 80° C. for 1 hour, successively. Then, the filter was subjected to plaque hybridization in substantially the same manner as mentioned above, except that the NDV HN gene labeled with [$^{32}$P]-deoxycytidine triphosphate prepared in substantially the same manner as in Step 3 was used as a probe. The stored agarose gel corresponding to the positive plaque on the filter which hybridized with the probe by the plaque hybridization was inoculated to a QEF culture which had been separately prepared in substantially the same manner as in Reference Example 4, followed by culturing. From the resultant culture, a recombinant virus was isolated in the same manner as mentioned before. The thus obtained recombinant virus was designated "HVT O1R strain".

Step 10

Detection of the HVT Antigen and the NDV HN Antigen Produced by the Recombinant HVT:

A suspension of cells infected with the recombinant virus HVT O1R strain obtained in Step 9 was prepared in substantially the same manner as in Step 4. The suspension was dropped on a slide glass which is adapted to be used in the fluorescent antibody technique. Then, the dropped suspension was spread, air-dried and treated with cold acetone for 10 minutes to fix the virus-infected cells on the slide glass. Then, whether or not both an HVT antigen and an NDV HN antigen were present in the cells fixed on the slide glass was examined by the indirect fluorescent antibody technique as follows. 0.5 ml of a primary antibody was put on the cells fixed on the slide glass and the reaction was conducted in a moist chamber at 37° C. for 30 minutes. As the primary antibody, an anti-NDV HN chicken antiserum was used. After completion of the reaction, the cells on the slide glass were washed with PBS three times. Then, 0.5 ml of an anti-chicken IgG antibody labeled with fluorescein isothiocyanate (4 staining units) as a secondary antibody was reacted with the cells and washed in substantially the same manner as mentioned above. A glycerin buffer solution (a mixture of 0.5M sodium carbonate-sodium hydrogen carbonate solution (pH 9.5) and non-fluorescence guaranteed grade glycerin, 1:9 by volume) was dropped on the cells and, then, the cells were covered with a cover slip. The thus obtained specimen was subjected to microscopic analysis by means of a fluorescence microscope (manufactured and sold by Nippon Kogaku K. K., Japan).

On the other hand, another slide glass, on which the cells infected with the recombinant virus HVT O1R strain were fixed, was prepared in the same manner as mentioned above, and the cells were subjected to analysis by the indirect fluorescent antibody technique in substantially the same manner as mentioned above except that an anti-HVT chicken antiserum was used as a primary antibody.

Figure 13:
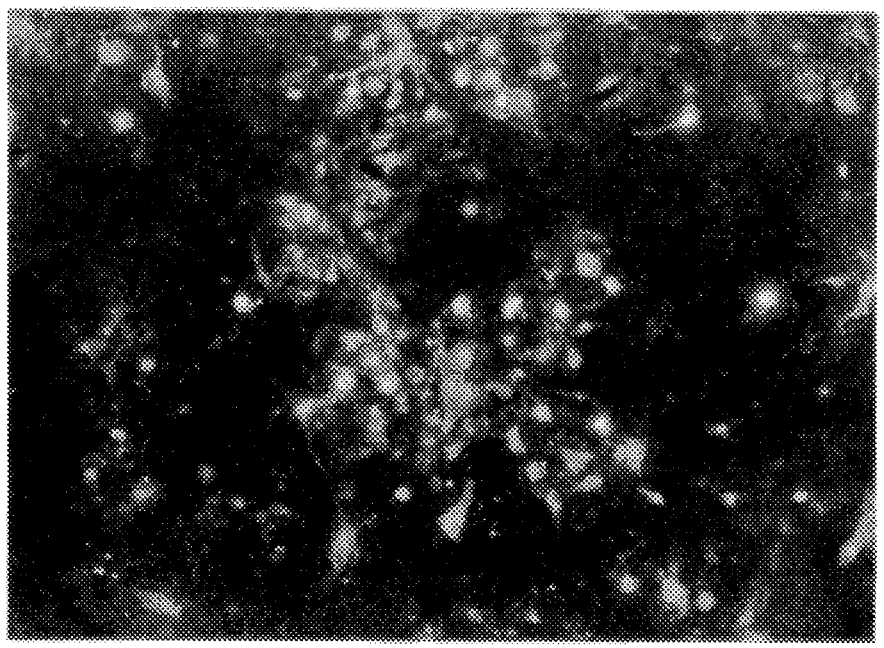
FIG. 13 is a photograph showing the result obtained by subjecting quail embryofibroblast (hereinafter referred to as "QEF") cells transfected with recombinant virus strain HVT O1R to immunoassay by indirect immunofluorescence technique in which anti-HVT gA antigen chicken antiserum is used as a primary antibody.
Figure 14:
FIG. 14 is a photograph showing the result obtained by subjecting QEF cells infected with recombinant virus strain HVT O1R to immunoassay by indirect immunofluorescence technique in which anti-NDV HN chicken antiserum is used as a primary antibody.

As a result, it was found that the recombinant virus HVT O1R strain produced both an HVT antigen and an NDV HN antigen. The photographs of the representative cells which were subjected to the above-mentioned analysis are shown in FIGS. 13 and 14.

EXAMPLE 2

Plasmid pNC-9 as prepared in Step 7 of Example 1 was digested with restriction enzyme HinfI. The resultant digest was treated with T4 DNA polymerase to convert both ends thereof to blunt ends. The resultant plasmid DNA was subjected to low-melting point agarose gel electrophoresis to obtain a DNA fragment of about 1.1 kb containing the HN gene of NDV.

Figure 7:
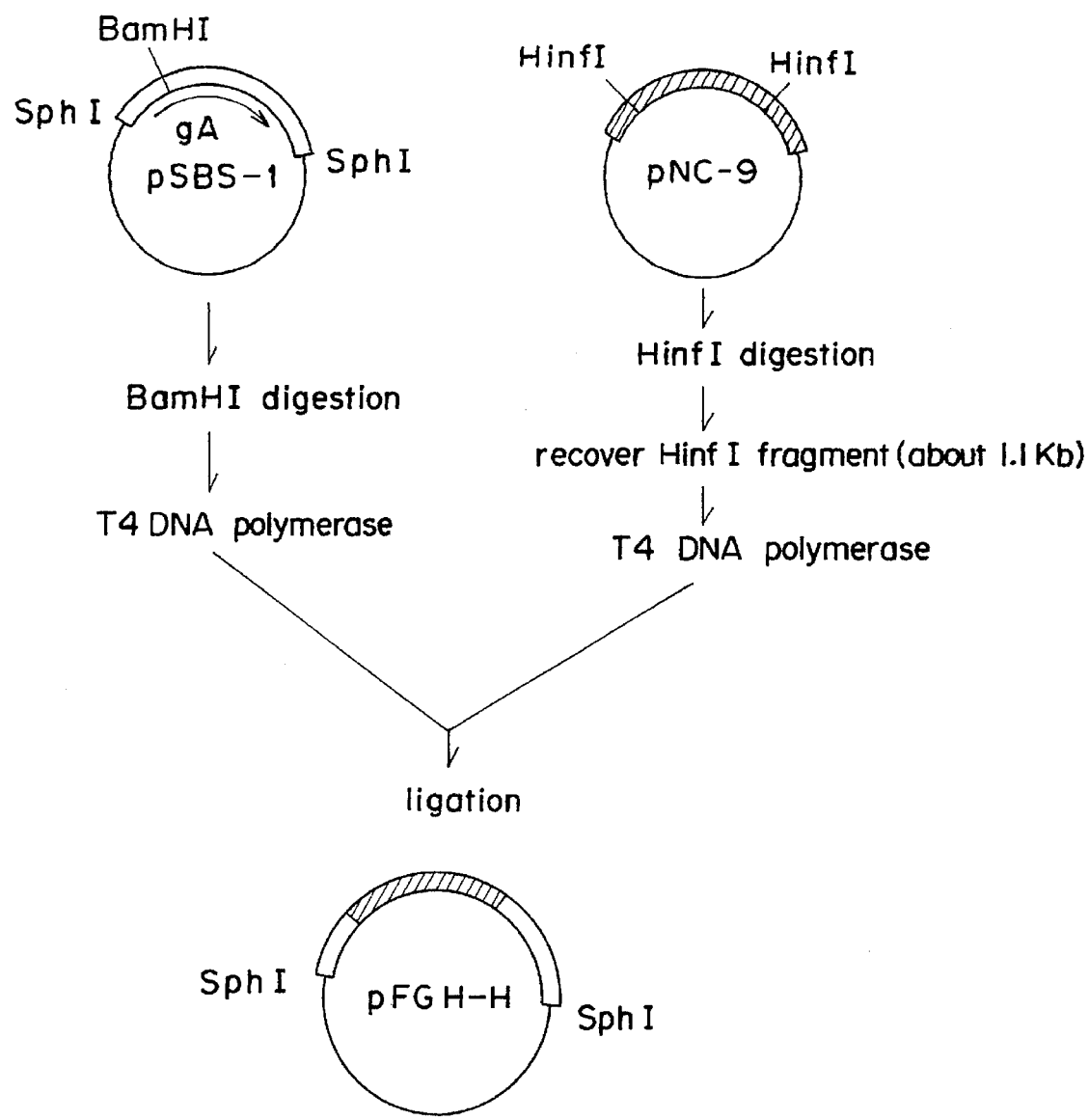
FIG. 7 shows a flow chart indicating the construction of plasmid pFGH-H comprising the gA antigen gene of HVT and a foreign gene, which plasmid is used for preparing a recombinant virus of the present invention capable of producing a fused protein.

On the other hand, plasmid pSBS-1 as obtained in Step 6 of Example 1 was cleaved by BamHI and treated with T4 DNA polymerase. To the thus obtained plasmid DNA, the above-obtained DNA fragment was ligated by means of T4 DNA ligase. With the resultant recombinant plasmid, cells of E. coli JM83 were transformed to form transformants. The above-obtained recombinant plasmid was designated "pFGH-H". The above procedure is illustrated in FIG. 7. In this plasmid, the HN gene of NDV was inserted in the DNA fragment containing the HVT gA antigen gene so that a fused protein of the HVT gA antigen and the NDV HN could be expressed.

Substantially the same procedure as in Step 9 of Example 1 was repeated except that the above-obtained plasmid pFGH-H was used instead of plasmid pHVT-1, to thereby obtain a recombinant virus. This recombinant virus was designated "HVT O1F strain".

Figure 15:
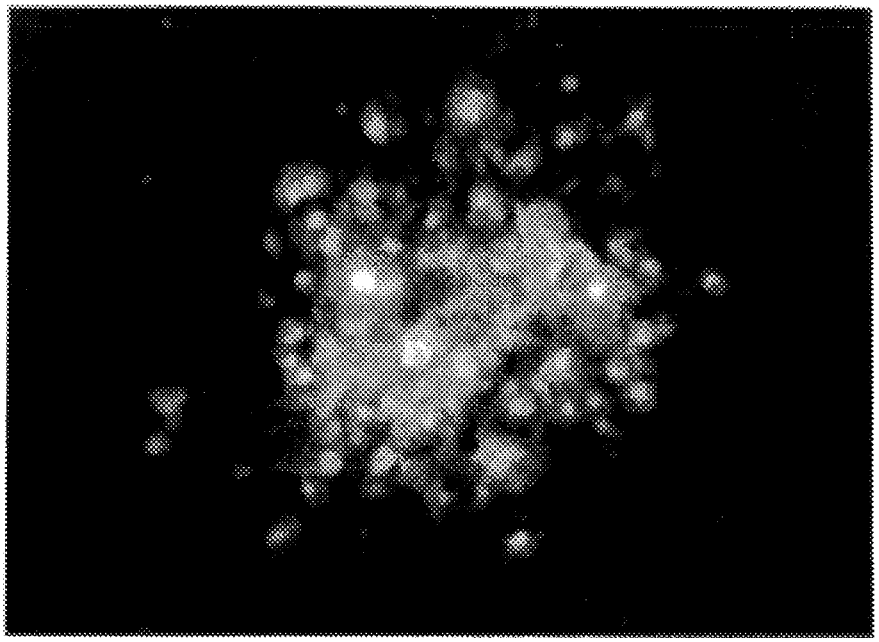
FIG. 15 is a photograph showing the result obtained by subjecting QEF cells infected with recombinant virus strain HVT O1F to immunoassay by indirect immunofluorescence technique in which anti-HVT gA antigen chicken antiserum is used as a primary antibody.
Figure 16:
FIG. 16 is a photograph showing the result obtained by subjecting QEF cells infected with recombinant virus strain HVT O1F to immunoassay by indirect immunofluorescence technique in which anti-NDV HN chicken antiserum is used as a primary antibody.

The thus obtained recombinant virus HVT O1F strain was subjected to analysis in substantially the same manner as in Step 10 of Example 1. Thus, it was confirmed that the recombinant virus produced both an HVT antigen and an NDV HN. The photograph of the representative cells subjected to the above-mentioned analysis are shown in FIGS. 14 and 15.

EXAMPLE 3

Step 1

Preparation of MDV Genomic DNA:

The genomic DNA of the MDV C2 strain was prepared in substantially the same manner as in Step 1 of Example 1 except that the QEF cells infected with the MDV C2 strain were used instead of the QEF cells infected with the HVT O1 strain.

Step 2

Cloning of Restriction Enzyme-Cleaved Fragments of the MDV Genomic DNA and Preparation of a Gene Library:

Substantially the same procedure as in Step 2 of Example 1 was repeated except that the MDV genomic DNA obtained in Step 1 of Example 3 was used instead of the HVT genomic DNA, to thereby obtain three gene libraries, that is, BamHI library, PstI library and HindIII library of MDV genomic DNA.

Step 3

Figure 8:
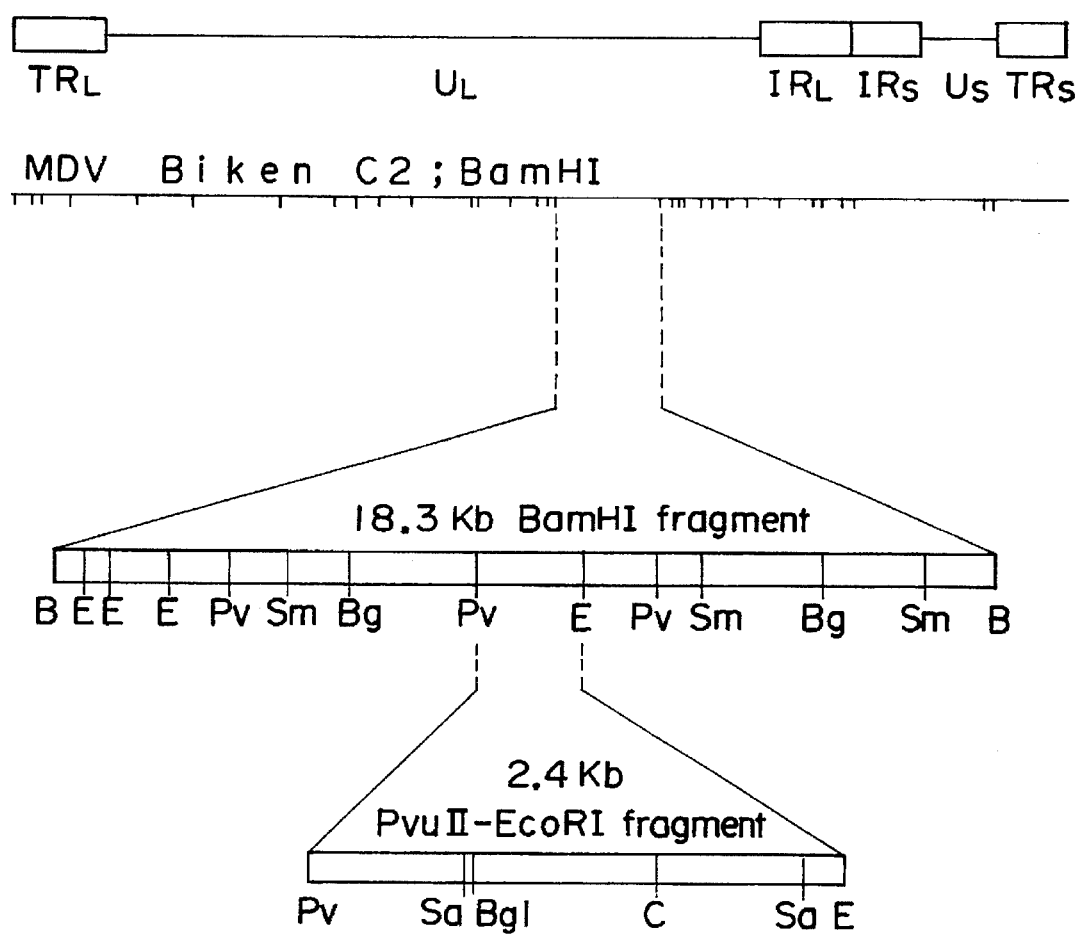
FIG. 8 shows a restriction map of the genomic DNA of MDV C2 strain.

Preparation of a Restriction Map of the Genomic DNA of MDV:

A restriction map of the genomic DNA of MDV was prepared in substantially the same manner as described in Step 3 of Example 1. The thus prepared restriction map is shown in FIG. 8. In FIG. 8, the abbreviations have the same meanings as those used in FIG. 1.

On the basis of the above-mentioned restriction map, a transformant clone containing a plasmid carrying a 18.3 kb BamHI fragment of the MDV genomic DNA was selected from the BamHI library prepared in the above Step 2. Subsequently, from the clone, the plasmid was isolated in the same manner as in Step 4 of Example 1. The plasmid was designated "pBam-B".

Step 4

Figure 9:
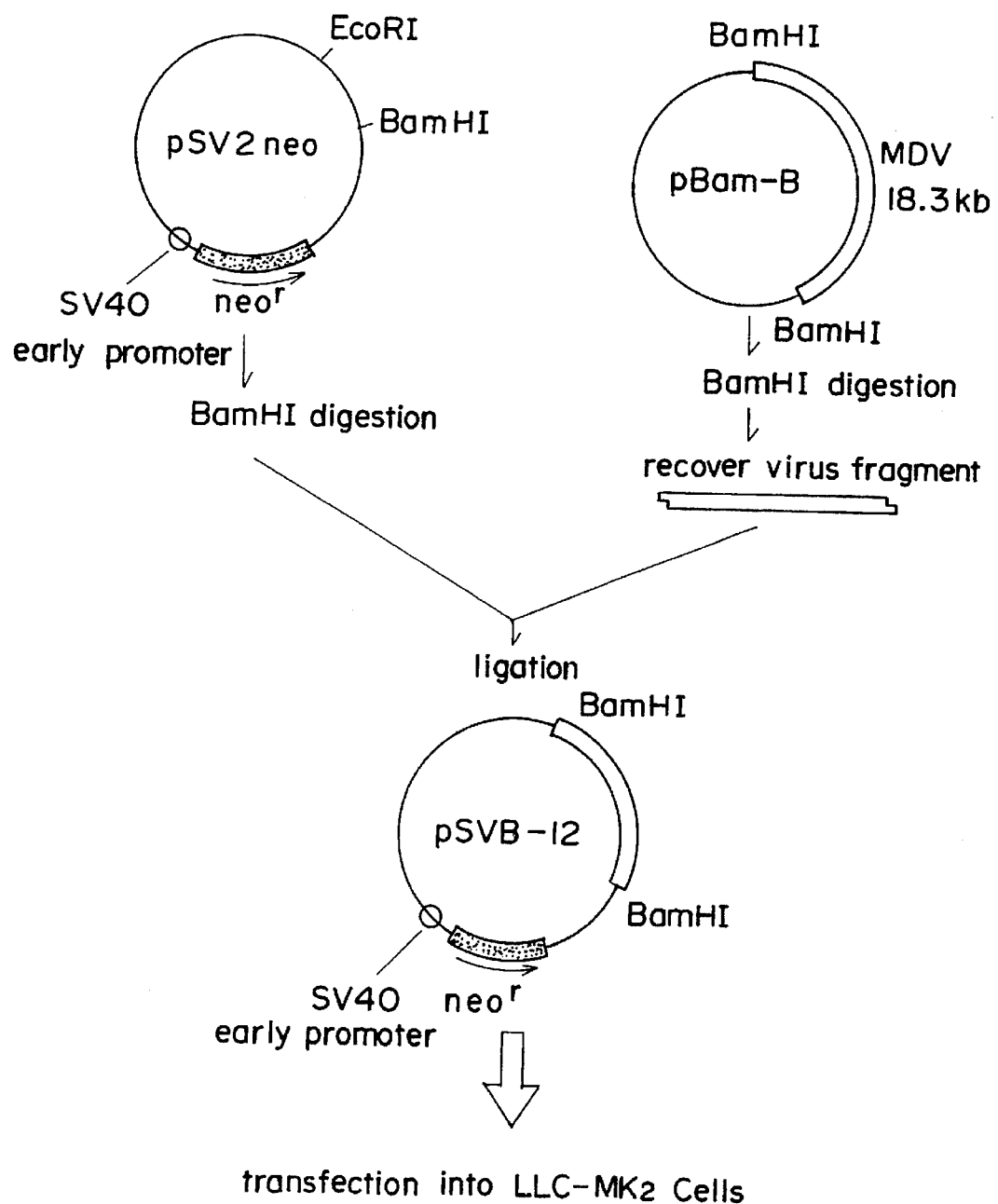
FIG. 9 shows a flow chart indicating the construction of an expression vector pSVB-12 for expressing the gA antigen gene of MDV.

Construction of an Expression Vector for Expressing the MDV gA Antigen Gene (a First Replication Vector):

In substantially the same manner as described in Step 4 of Example 1, the 18.3 kb BamHI fragment of the plasmid pBam-B obtained in the above Step 3 was inserted in plasmid pSV2-neo at the BamHI site thereof, thereby obtaining plasmid pSVB-12. This procedure is illustrated in FIG. 9.

Further, on the basis of the restriction map prepared in Step 3 of Example 3, an EcoRI-PvuII fragment of about 2.2 kb was cut off from the 18.3 kb BamHI fragment region of the plasmid pBam-B in substantially the same manner as described in Step 2 of Example 1. Using the thus obtained EcoRI-PvuII fragment, plasmid pBEP-22 was constructed in substantially the same manner as described in Step 4 of Example 1.

Step 5

Figure 19:
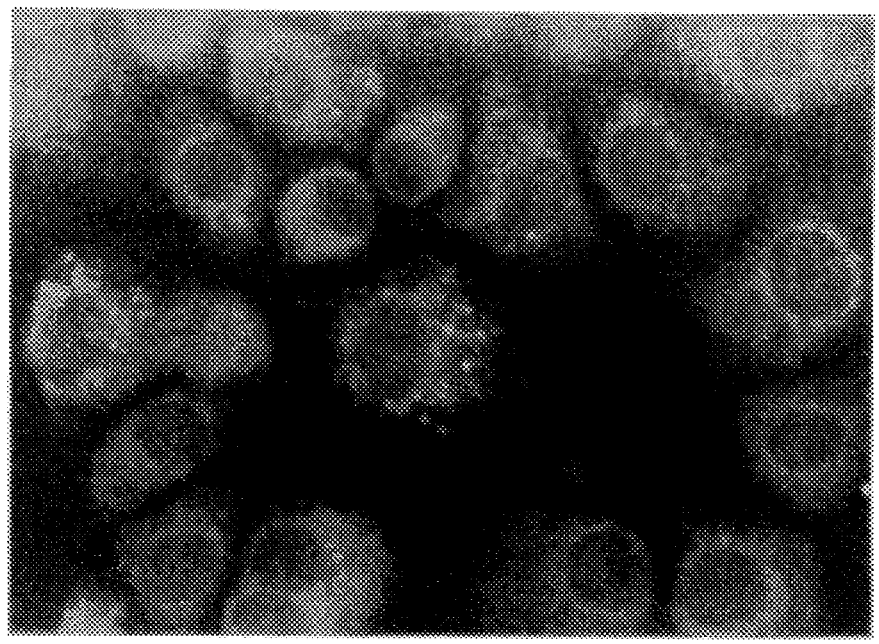
FIG. 19 is a photograph showing the result obtained by subjecting LLC-MK$_2$ cells transformed with plasmid pBEP-22 and capable of producing gA antigen, to immunoassay by avidin-biotin immunofluorescence technique.

Transformation of a Mammalian Cell with Plasmid pBEP-22 and Detection of the MDV gA Antigen:

A simian kidney cell LLC-MK$_2$ was transformed with the plasmid pBEP-22, and the resultant transformant was cultured in substantially the same manner as described in Step 5 of Example 1. Whether or not an MDV gA antigen was produced in the transformant was also analyzed in accordance with the immunofluorescence technique as mentioned in Step 5 of Example 1. As a result, the production of an MDV gA antigen by the transformant obtained above was confirmed (see FIG. 19). Subsequently, the plasmid pBEP-22 capable of expressing the MDV gA antigen gene, which was obtained in Step 4 of Example 3, was digested with restriction enzymes in substantially the same manner as in Step 6 of Example 1, thereby obtaining an EcoRI-PvuII fragment of about 2.2 kb containing a gene coding for the gA antigen gene of MDV. The nucleotide sequence of the fragment was determined according to the dideoxy chain termination method. The nucleotide sequence of the gA antigen gene and the amino acid sequence deduced therefrom are shown in FIGS. 3(a) to 3(k).

Step 6

Figure 10:
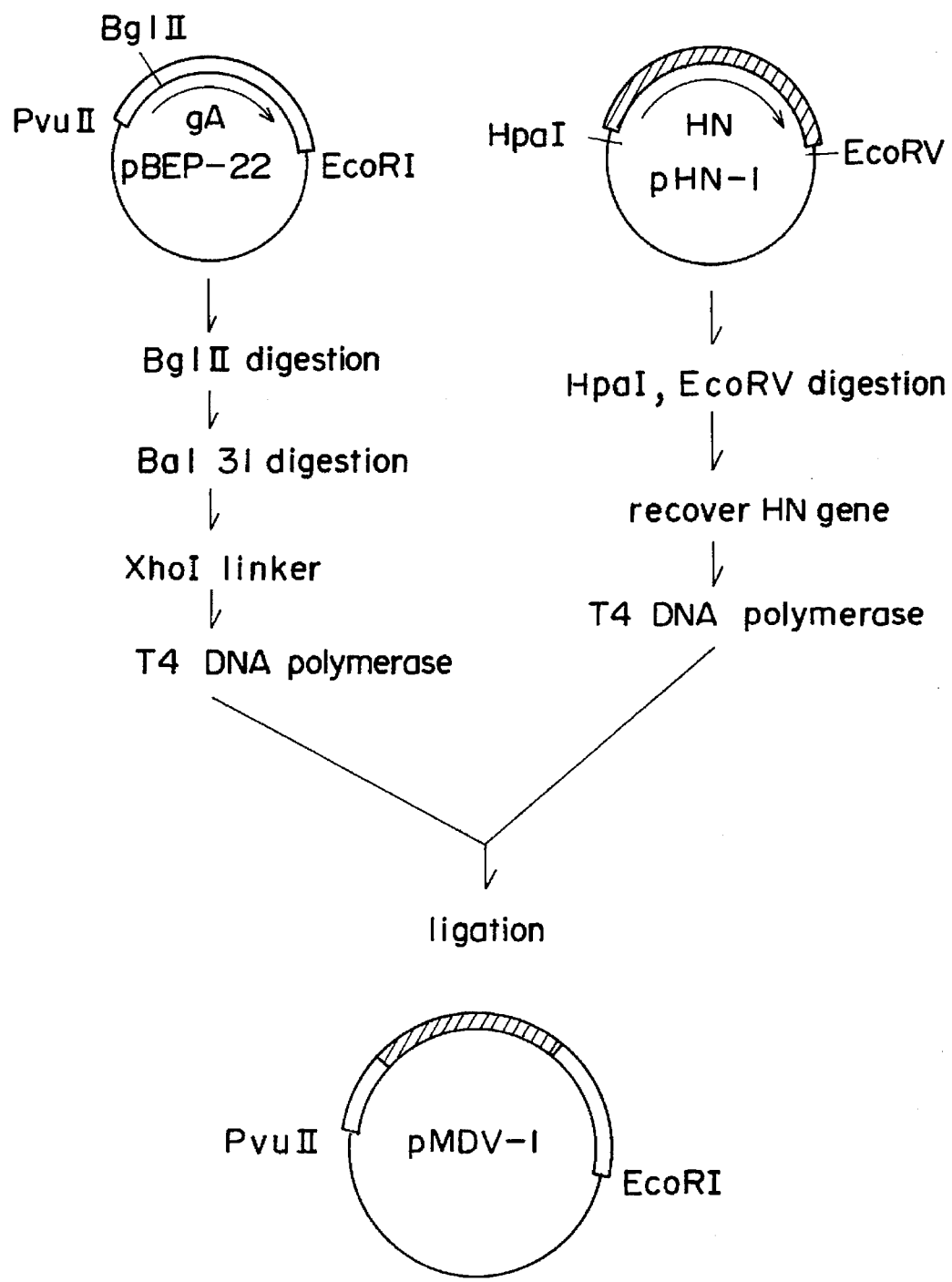
FIG. 10 shows a flow chart indicating the construction of plasmid pMDV-1 comprising the gA antigen gene of MDV and a foreign gene, which plasmid is used for preparing a recombinant virus of the present invention.

Construction of a Second Replication Vector Containing the MDV gA Antigen Gene and a Foreign Gene (HN Gene):

Plasmid pMDV-1 was constructed using the plasmid pHN-1 obtained in Step 7 of Example 1 and the plasmid pBEP-22 obtained in Step 4 of Example 3 in substantially the same manner as in Step 8 of Example 1. The construction of plasmid pMDV-1 is diagramatically illustrated in FIG. 10.

Step 7

Preparation of a Recombinant MDV:

Substantially the same procedure as described in Step 9 of Example 1 was repeated except that the MDV C2 strain was used instead of the HVT O1 strain and plasmid pMDV-1 was used instead of plasmid pHVT-1, to obtain a recombinant virus. The thus obtained recombinant virus was designated "MDV C2R strain".

Step 8

Detection of the MDV Antigen and the NDV HN Antigen Produced by the Recombinant MDV:

Detection of the MDV antigen and the NDV HN antigen produced in the QEF cells infected with the recombinant virus MDV C2R strain was performed according to the indirect fluorescent antibody technique as described in Step 10 of Example 1. As the primary antibodies, there were employed an anti-NDV HN antigen chicken antiserum and an anti-MDV antigen chicken antiserum. As a result, the simultaneous production of the MDV antigen and the NDV HN antigen by the above-mentioned recombinant virus strain was confirmed. The photographs of the representative cells subjected to the above-mentioned analysis are shown in FIGS. 20 and 21.

EXAMPLE 4

Figure 11:
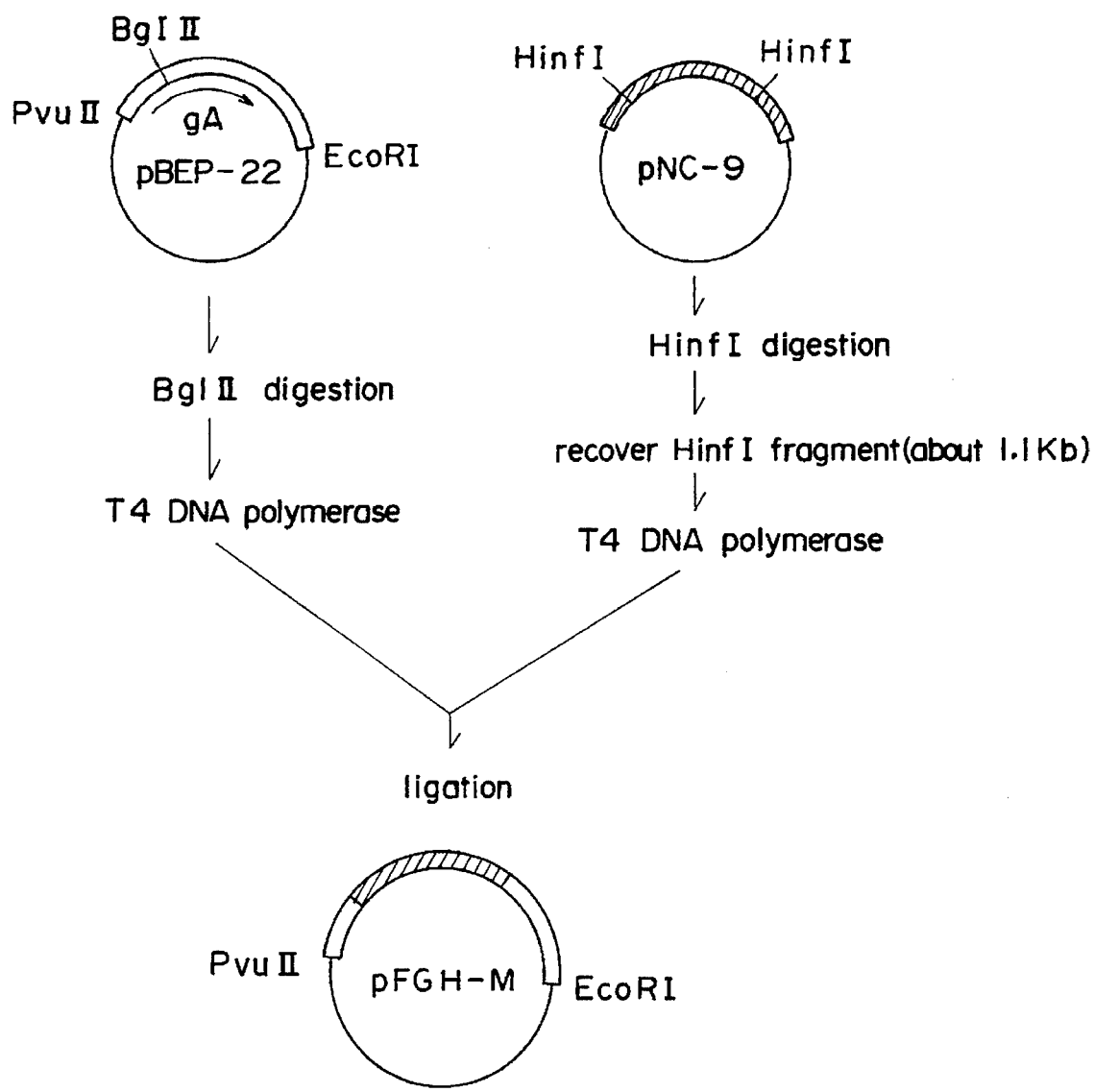
FIG. 11 shows a flow chart indicating the construction of plasmid pFGH-M comprising the gA antigen gene of MDV and a foreign gene, which plasmid is used for preparing a recombinant virus of the present invention capable of producing a fused protein.
Figure 12:
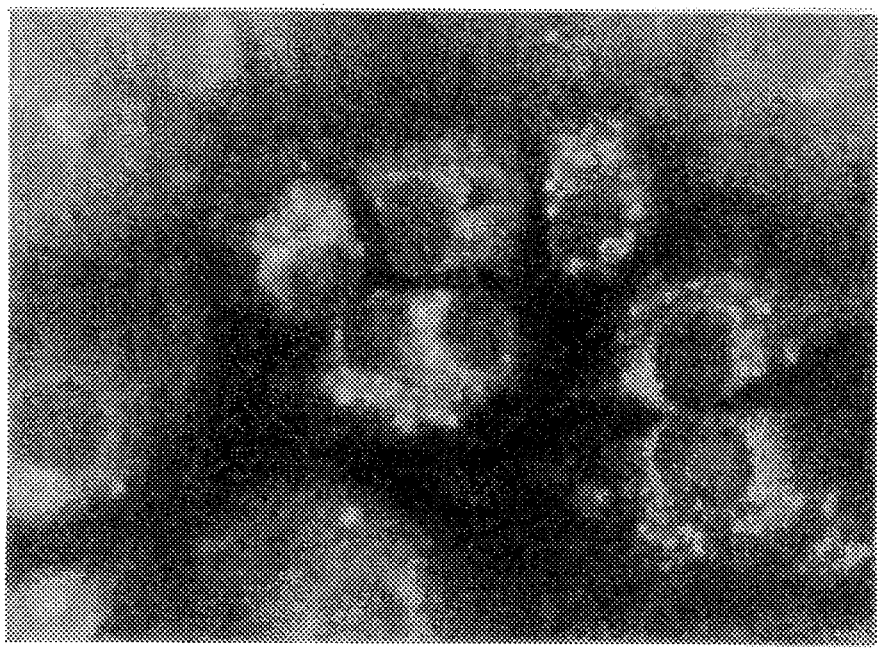
FIG. 12 is a photograph showing the result obtained by subjecting LLC-MK$_2$ cells transformed with plasmid pSVB52-3 and capable of producing the gA antigen of HVT, to immunoassay by avidin-biotin immunofluorescence technique.

Substantially the same procedure as in Step 6 of Example 3 was repeated except that plasmid pNC-9 obtained in Step 7 of Example 1 was used instead of plasmid pHN-1, to thereby obtain a second replication vector designated "plasmid pFGH-M". The construction of plasmid pFGH-M is diagramatically illustrated in FIG. 11. This plasmid is capable of expressing an MDV gA antigen gene and an NDV HN gene so that a fused protein of the MDV gA antigen and the NDV HN is produced.

Then, substantially the same procedure as in Step 7 of Example 3 was repeated except that the plasmid pFGH-M was used instead of plasmid pMDV-1, to thereby obtain a recombinant virus. The recombinant virus was designated "MDV C2F strain".

By the analysis in the same manner as in Step 10 of Example 1, it was confirmed that the recombinant virus MDV C2F strain produced both an MDV antigen and an NDV HN.

EXAMPLE 5

Substantially the same procedure as in Step 9 of Example 1 was repeated except that plasmid pMDV-1 obtained in Step 6 of Example 3 was used instead of plasmid pHVT-1, to thereby obtain a recombinant virus. The recombinant virus was designated "HVT O1MH strain".

Figure 17:
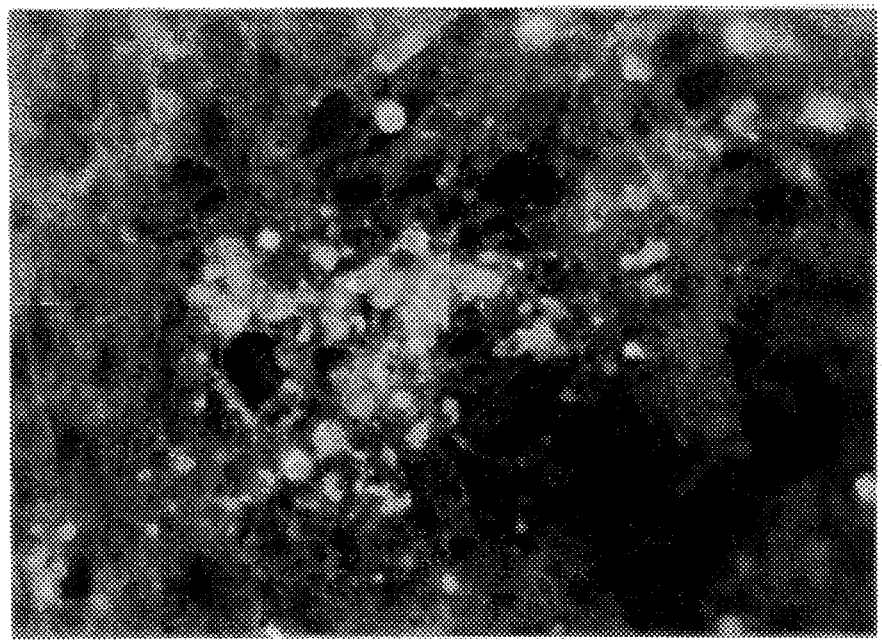
FIG. 17 is a photograph showing the result obtained by subjecting QEF cells infected with recombinant virus strain HVT O1FMH to immunoassay by indirect immunofluorescence technique in which anti-HVT gA antigen chicken antiserum is used as a primary antibody.
Figure 18:
FIG. 18 is a photograph showing the result obtained by subjecting QEF cells infected with recombinant virus strain HVT O1FMH to immunoassay by indirect immunofluorescence technique in which anti-NDV HN chicken antiserum is used as a primary antibody.

By the analysis in the same manner as in Step 10 of Example 1, it was confirmed that the recombinant virus HVT O1MH strain produced both an HVT antigen and an NDV HN. The results of the analysis were photographed and are shown in FIGS. 17 and 18.

EXAMPLE 6

Substantially the same procedure as in Step 9 of Example 1 was repeated except that plasmid pFGH-M obtained in Example 4 was used instead of plasmid pHVT-1, to thereby obtain a recombinant virus. The recombinant virus was designated "HVT O1FMH strain". By the analysis in the same manner as in Step 10 of Example 1, it was confirmed that the recombinant virus HVT O1FMH strain produced both an HVT antigen and an NDV HN. The results of the analysis were photographed and are shown in FIGS. 20 and 21.

EXAMPLE 7

Substantially the same procedure as in Step 7 of Example 3 was repeated except that plasmid pHVT-1 obtained in Step 6 of Example 1 was used instead of plasmid pHVT-1, to thereby obtain a recombinant virus. The recombinant virus was designated "MDV C2HH strain".

By the analysis in the same manner as in Step 10 of Example 1, it was confirmed that the recombinant virus MDV C2HH strain produced both an MDV antigen and an NDV HN.

EXAMPLE 8

Substantially the same procedure as in Step 7 of Example 3 was repeated except that plasmid pFGH-H obtained in Example 2 was used instead of plasmid pMDV-1, to thereby obtain a recombinant virus. The recombinant virus was designated "MDV C2FHH strain". By the analysis in the same manner as in Step 10 of Example 1, it was confirmed that the recombinant virus MDV C2FHH strain produced both an MDV antigen, and an NDV HN.

EXAMPLE 9

Preparation of a Recombinant MDV Containing a Spike Protein Gene of Avian Infectious Bronchitis Virus as a Foreign Gene:

Step 1

A cDNA library of the genomic DNA of an avian infectious bronchitis virus (hereinafter referred to as "IBV") strain M41 (which is commercially available from Japanese Association of Veterinary Biologics, Japan) was prepared in substantially the same manner as described in Step 7 of Example 1 except that the IBV M41 strain was used instead of the NDV FUDAI strain. Based on the gene map of the IDV and the nucleotide sequence of the gene coding for spike protein antigen (hereinafter referred to as "SP antigen") of the IDV (Journal of General Virology, 16, 719–726, 1985), a plasmid carrying a DNA fragment containing the SP antigen gene was cloned from the cDNA library. The cloned plasmid was designated "pSP-922". The plasmid pSP-922 was cleaved by restriction enzymes XbaI and HindIII and digested with nuclease Bal31, to thereby obtain a DNA fragment containing the SP antigen gene. Then, substantially the same procedure as in Step 8 of Example 1 was repeated except that the above-obtained DNA fragment was used instead of the DNA fragment containing the NDV HN gene, to thereby obtain a plasmid comprising the promoter of an HVT gA antigen gene and the SP antigen gene ligated downstream thereof. This plasmid was designated "pHVSP-3".

Step 2

Using the thus obtained plasmid pHVSP-3 and the HVT O1 strain, a recombinant virus was prepared in substantially the same manner as in Step 9 of Example 1. The prepared recombinant virus was designated "HVT O1HS strain". By the analysis according to the same method as in Step 10 of Example 1 except that an anti-IBV antigen chicken antiserum was used as a secondary antibody instead of the anti-NDV HN chicken antiserum, it was confirmed that the thus obtained recombinant virus produced both an HVT antigen and an IBV SP antigen.

EXAMPLE 10

Step 1

Substantially the same procedure as in Step 9 of Example 1 was repeated except that DNA fragment containing the IBV SP antigen gene was used instead of the DNA fragment containing the NDV HN gene and that plasmid pBEP-22 obtained in Step 4 of Example 3 was used instead of plasmid pSBS-1 obtained in Step 6 of Example 1, to thereby obtain a plasmid comprising the promoter of an MDV gA antigen gene and the SP antigen gene ligated downstream thereof. This plasmid was designated "pMDSP-22".

Step 2

Using the thus obtained plasmid pMDSP-22 and the HVT O1 strain, a recombinant virus was prepared in substantially the same manner as in Step 9 of Example 1. The prepared recombinant virus was designated "HVT O1MS strain". By the analysis according to the same method as in Step 10 of Example 1 except that an anti-IBV antigen chicken antiserum was used as a primary antibody instead of the anti-NDV HN chicken antiserum, it was confirmed that the thus obtained recombinant virus produced both an HVT antigen and an IBV SP antigen.

EXAMPLE 11

Using the plasmid pHVSP-3 obtained in Example 9 and the MDV C2 strain, a recombinant virus was prepared in substantially the same manner as in Step 9 of Example 1. The prepared recombinant virus was designated "MDV C2HS strain". By the analysis according to the same method as in Step 10 of Example 1 except that an anti-IBV antigen chicken antiserum was used as a primary antibody instead of the anti-NDV HN chicken antiserum, it was confirmed that the thus obtained recombinant virus produced both an MDV antigen and an IBV SP antigen.

EXAMPLE 12

Using the plasmid pMDSP-22 obtained in Example 10 and the MDV C2 strain, a recombinant virus was prepared in substantially the same manner as in Step 9 of Example 1. The prepared recombinant virus was designated "MDV C2MS strain". By the analysis according to the same method as in Step 10 of Example 1 except that an anti-IBV antigen chicken antiserum was used as a primary antibody instead of the anti-NDV HN chicken antiserum, it was confirmed that the thus obtained recombinant virus produced both an MDV antigen and an IBV SP antigen.

EXAMPLE 13

Production of a Bivalent Live Vaccine Containing a Recombinant Marek's Disease Virus as an Active Ingredient and Assay of the Safety and Activity of the Bivalent Live Vaccine:

Virus-infected QEF cells were prepared in accordance with the method described in Reference Example 4, using as a seed virus each of the recombinant virus strains HVT O1R, HVT O1F, HVT O1MH, HVT O1FMH, MDV C2R, MDV C2F, MDV C2HH and MDV C2FHH obtained in Examples 1 to 8. QEF cells infected with each of the above-mentioned recombinant virus strains were cultured in 50 Roux bottles each having a volume of 1 liter. After completion of the culturing, the infected cells were detached from the inner wall of each of the bottles by the use of a trypsin solution prepared by dissolving $Na_2$-EDTA in the solution obtained in Reference Example 2 in a concentration of 0.02 w/v %, and suspended in the trypsin solution. The suspensions containing the cells infected with the recombinant HVT strains were subjected to ultrasonic treatment, and the resultant supernatants were collected. As a result, from each of the recombinant HVT strains, there was obtained about 500 ml of a bivalent live vaccine concentrate effective to Marek's disease and Newcastle disease. On the other hand, with respect to the suspensions containing the cells infected with the recombinant MDV strains, 500 ml of each of the suspensions was taken and used as a bivalent live vaccine concentrate. From each of the thus obtained concentrates, 50 ml was sampled. The samples were subjected to the tests mentioned below. The rest of each of the concentrates was diluted with the buffer containing a stabilizer as mentioned in Step 9 of Example 1, so as to adjust the virus content to 1,000 PFU. From each of the thus obtained dilutions, 5 l was taken and put into 100 ml-vials. The vials were sealed with stoppers, and stored at –70° C. With respect to the dilutions containing the recombinant HVT strains, twenty vials of the dilution containing each of the recombinant HVT strains were subjected to lyophilization, sealed with stoppers, and stored at 4° C. From each of the thus obtained vial groups, four vials were sampled at random and, along with the above-mentioned live vaccine concentrates, were subjected to the following tests. That is, in order to evaluate the competence of each live vaccine, i.e. the safety, effectiveness, homogeneity and storage stability thereof, the samples were subjected to the tests relating to "dried Marek's disease live vaccine", "frozen Marek's disease live vaccine" and "live Newcastle disease vaccine" as prescribed in Standards on Biological Preparations for Animals (Notification No. 599 from the Ministry of Agriculture, Forestry and Fisheries, Japan). As a result, it was found that the vaccines obtained by the above-described procedure had satisfactory competence as a bivalent live vaccine. The vaccines were subjected to the clinical tests described in Example 14 below, as a liquid vaccine containing the HVT O1R strain (hereinafter referred to as "liquid rHVT") and a dried vaccine containing the same (hereinafter referred to as "dried rHVT"); a liquid vaccine containing the HVT O1F strain (hereinafter referred to as "liquid rHVT-F") and a dried vaccine containing the same (hereinafter referred to as "dried rHVT-F"); a liquid vaccine containing the HVT O1MH strain (hereinafter referred to as "liquid rHVT-MH") and a dried vaccine containing the same (hereinafter referred to as "dried rHVT-MH"); a liquid vaccine containing the HVT O1FMH strain (hereinafter referred to as "liquid rHVT-FMH"); and a dried vaccine containing the same (hereinafter referred to as "dried rHVT-FMH"); a liquid vaccine containing the MDV C2R strain (hereinafter referred to as "liquid rMDV"); a liquid vaccine containing the MDV C2F strain (hereinafter referred to as "liquid rMDV-F"); a liquid vaccine containing the MDV C2HH strain (hereinafter referred to as "liquid rMDV-HH"); and a liquid vaccine containing the MDV C2FHH strain (hereinafter referred to as "rMDV-FHH").

EXAMPLE 14

Immunogenicity and Immune Effect of the Bivalent Live Vaccines Containing Recombinant Virus Strains:

In order to evaluate the field efficacy of the vaccines produced in Example 13, clinical tests were performed as follows. 90 one-day-old SPF chicks were procured, and divided into five groups consisting of Groups A–D each composed of 20 chicks and Group E composed of 10 chicks. The vaccines were intramuscularly injected into the lower limb of the chicks of Groups A–C and Group E. No vaccine was injected into the chicks of Group D so as to use these chicks as a control. The particulars of the vaccine injection into the chicks were as follows. The liquid rHVT vaccine was injected into the chicks of Group A in an amount of 2 ml/chick; the dried rHVT vaccine, into the chicks of Group B in an amount of 2 ml/chick; the liquid rMDV vaccine, into the chicks of Group C in an amount of 1 ml/chick; and the liquid live vaccine HVT O1 produced using the HVT O1 strain as a seed virus according to the procedure described in Example 13, into the chicks of Group E in an amount of 2 ml/chick. Each group was isolated from the other groups, and the chicks were reared under observation. Three weeks after the injection of the vaccines, blood was collected from the wing veins of each of the chicks so as to obtain 1 ml of serum sample per chick. The serum samples were subjected to an assay of antibody titer in order to evaluate the immunogenicity of each of the vaccines. In the assay of antibody titer, each of the serum samples was subjected to doubling dilution using the PBS obtained in Reference Example 1, and the examination for determining whether or not the serum reacts with the HVT and MDV antigens was performed in accordance with the indirect fluorescent antibody technique as described in Step 10 of Example 1, while the examination for determining whether or not the serum reacts with the NDV antigen was performed according to the customary hemagglutination inhibition test in which a 0.5 v/v % chicken erythrocyte suspension and a hemag-glutinin of the NDV Ishii strain (commercially available from Japanese Association of Veterinary Biologics, Japan) were used. The antibody titer of each vaccine was defined as the geometric mean of the maximum dilution degrees of the samples, which is obtained by calculating the 20th (in the cases of Groups A–C) or 10th root (in the case of Group E) of the product of the maximum dilution degrees of the samples, at which maximum dilution the positive reaction was observed in the above assay.

Further, chicks were subjected to a test for determining the immune effect of each vaccine, in which the chicks were attacked by a virulent virus. First, Groups A–C and E each composed of 20 chicks were divided into subgroups each composed of 10 chicks. That is, Groups A, B, C and E were respectively divided into Subgroups A-a and A-b, B-a and B-b, C-a and C-b, and E-a and E-b each composed of 10 chicks. The chicks of Subgroups A-a, B-a, C-a and E-a, totalling 40 chicks, were intramuscularly injected individually with the virulent virus NDV SATO strain in an amount of 10 $TCID_{50}$/chick which was a lethal dose of the strain. With respect to the amount, $TCID_{50}$ represents a quantity by which 50% of cultured tissue is infected. On the other hand, the chicks of Subgroups A-b, B-b, C-b and E-b along with Group D, totaling 50 chicks, were intramuscularly injected individually with the virulent virus MDV·JM strain (commercially available from National Veterinary Assay Laboratory, Japan) in an amount of 10 PFU/chick. Each of the subgroups of each group was isolated from the others, and the chicks challenged by the virulent viruses were reared under observation. With respect to the chicks challenged by the virulent virus NDV SATO strain, the mortality for each of the subgroups was determined two weeks after the challenge of the chicks by the virus. On the other hand, with respect to the chicks challenged by the virulent virus MDV·JM strain, the neurovirulence for each of the subgroups of each group was determined, five weeks after the challenge of the chicks by the virus, by the diagnosis made on the basis of examination as to paralysis and convulsion symptoms, autopsy and microscopic observation of pathological tissues. The results are shown in Table 1. From the results, it was confirmed that all of the rHVT and rMDV vaccines produced in Example 13 had excellent immunogenicity and exhibited excellent infection preventing effect.

Moreover, with respect to the other bivalent live vaccines produced in Example 13 also, the clinical tests as described above were performed, and the results are shown in Tables 2 to 4. From the results, it was confirmed that the above-mentioned other bivalent live vaccines also had excellent immunogenicity and exhibited excellent infection preventing effect.

TABLE 1

| Live vaccine-inoculated groups | The Number of chickens tested | Antibody titer[1] | | Challenge test | |
|---|---|---|---|---|---|
| | | NDV | HVT | Virus | Mortality[2] Morbidity[3] |
| Liquid rHVT Group | | 29.9 | 1194 | | |
| A - a | 10 | | | NDV | 0/10 |
| A - b | 10 | | | MDV | 0/10 |
| Dry rHVT Group | | 30.4 | 1214 | | |
| B - a | 10 | | | NDV | 0/10 |
| B - b | 10 | | | MDV | 0/10 |
| Liquid rMDV Group | | 33.1 | 1114 | | |
| C - a | 10 | | | NDV | 0/10 |
| C - b | 10 | | | MDV | 0/10 |
| HVT O1 | | <4 | 1180 | | |
| Group D | 10 | | | MDV | 0/10 |
| Control (not inoculated) Group | | <4 | <20 | | |
| E - a | 10 | | | NDV | 10/10 |
| E - b | 10 | | | MDV | 10/10 |

TABLE 1-continued

| Live vaccine-inoculated groups | The Number of chickens tested | Antibody titer[1] NDV | Antibody titer[1] HVT | Challenge test Virus | Challenge test Mortality[2] Morbidity[3] |
|---|---|---|---|---|---|

Note:
[1] Geometric mean of the titers obtained with respect to 20 chickens of each group by the hemagglutination inhibition test in the case of the use of NDV and by the indirect fluorescent antibody method in the case of the use of MDV.
[2] Mortality (in the case of the use of NDV) is indicated by the formula B/A, wherein A is the number of chickens tested, B is the number of chickens died.
[3] Morbidity (in the case of the use of MDV) is indicated by the formula C/A, wherein A has the same meaning as mentioned above, C is the number of chickens which have a positive lesion of nerve.

TABLE 2

| Live vaccine-inoculated groups | The Number of chickens tested | Antibody titer[1] NDV | Antibody titer[1] HVT | Challenge test Virus | Challenge test Mortality[2] Morbidity[3] |
|---|---|---|---|---|---|
| Liquid rHVT-F Group |  | 32.0 | 1084 |  |  |
| A - a | 10 |  |  | NDV | 0/10 |
| A - b | 10 |  |  | MDV | 0/10 |
| Dry rHVT-F Group |  | 31.2 | 1280 |  |  |
| B - a | 10 |  |  | NDV | 0/10 |
| B - b | 10 |  |  | MDV | 0/10 |
| Liquid rMDV-F Group |  | 35.3 | 1318 |  |  |
| C - a | 10 |  |  | NDV | 0/10 |
| C - b | 10 |  |  | MDV | 0/10 |
| HVT O1 |  | <4 | 1200 |  |  |
| Group D | 10 |  |  | MDV | 0/10 |
| Control (not inoculated) Group |  | <4 | <20 |  |  |
| E - a | 10 |  |  | NDV | 10/10 |
| E - b | 10 |  |  | MDV | 10/10 |

Note: [1], [2] and [3] have the same meanings as in Table 1.

TABLE 3

| Live vaccine-inoculated groups | The Number of chickens tested | Antibody titer[1] NDV | Antibody titer[1] HVT | Challenge test Virus | Challenge test Mortality[2] Morbidity[3] |
|---|---|---|---|---|---|
| Liquid rHVT-MH Group |  | 24.0 | 1280 |  |  |
| A - a | 10 |  |  | NDV | 0/10 |
| A - b | 10 |  |  | MDV | 0/10 |
| Dry rHVT-MH Group |  | 28.5 | 1350 |  |  |
| B - a | 10 |  |  | NDV | 0/10 |
| B - b | 10 |  |  | MDV | 0/10 |
| Liquid rMDV-MH Group |  | 20.3 | 990 |  |  |
| C - a | 10 |  |  | NDV | 0/10 |
| C - b | 10 |  |  | MDV | 0/10 |
| HVT O1 |  | <4 | 1150 |  |  |
| Group D | 10 |  |  | MDV | 0/10 |
| Control (not inoculated) Group |  | <4 | <20 |  |  |
| E - a | 10 |  |  | NDV | 10/10 |
| E - b | 10 |  |  | MDV | 10/10 |

Note: [1], [2] and [3] have the same meanings as in Table 1.

TABLE 4

| Live vaccine-inoculated groups | The Number of chickens tested | Antibody titer[1] NDV | Antibody titer[1] HVT | Challenge test Virus | Challenge test Mortality[2] Morbidity[3] |
|---|---|---|---|---|---|
| Liquid rHVT-FMH Group |  | 23.2 | 1140 |  |  |
| A - a | 10 |  |  | NDV | 0/10 |
| A - b | 10 |  |  | MDV | 0/10 |
| Dry rHVT-FMH Group |  | 25.8 | 1090 |  |  |
| B - a | 10 |  |  | NDV | 0/10 |
| B - b | 10 |  |  | MDV | 0/10 |
| Liquid rMDV-FMH Group |  | 31.4 | 880 |  |  |
| C - a | 10 |  |  | NDV | 0/10 |
| C - b | 10 |  |  | MDV | 0/10 |
| HVT O1 |  | <4 | 1080 |  |  |
| Group D | 10 |  |  | MDV | 0/10 |
| Control (not inoculated) Group |  | <4 | <20 |  |  |
| E - a | 10 |  |  | NDV | 10/10 |
| E - b | 10 |  |  | MDV | 10/10 |

Note: [1], [2] and [3] have the same meanings as in Table 1.

What is claimed is:

1. A recombinant virus comprising the genomic DNA of an attenuated virus of Marek's disease or a herpes virus of turkeys and at least one foreign gene selected from the group consisting of a Newcastle disease virus gene and an avian infectious bronchitis virus gene, wherein said attenuated virus of Marek's disease or said herpes virus of turkeys is selected from the group consisting of a Marek's disease virus BIKEN "C2" strain and a herpes virus of turkeys BIKEN "O1" strain, each respectively having a glycoprotein A antigen gene represented by one of the entire nucleotide sequences shown in FIGS. 3(*a*) through 3(*k*) hereof, and wherein said foreign gene is operably linked in a correct reading frame of said genomic DNA downstream of a promoter of a glycoprotein A antigen gene of said genomic DNA, wherein said recombinant virus elicits a protective host immune response to infection with Marek's disease virus.

2. The recombinant virus according to claim 1, wherein said Newcastle disease virus gene is a gene coding for hemagglutinin and neuraminidase of Newcastle disease virus.

3. The recombinant virus according to claim 1, wherein said avian infectious bronchitis virus gene is a spike protein gene of avian infectious bronchitis virus.

4. A recombinant virus vaccine which elicits a protective immune response to Marek's disease virus comprising:

an immunogenically effective amount of a recombinant virus comprising the genomic DNA of an attenuated virus of Marek's disease or a herpes virus of turkeys and at least one foreign gene selected from the group consisting of a Newcastle disease virus gene and an avian infectious bronchitis virus gene, wherein said attenuated virus of Marek's disease or said herpes virus of turkeys is selected from the group consisting of a Marek's disease virus BIKEN "C2" strain and a herpes virus of turkeys BIKEN "O1" strain, each respectively having a glycoprotein A antigen gene represented by one of the entire nucleotide sequences shown in FIGS. 3($a$) through 3($k$) hereof, and wherein said foreign gene is operably linked in a correct reading frame of said genomic DNA downstream of a promoter of a glycoprotein A antigen gene of said genomic DNA, Wherein said foreign gene is expressed in infected cells, and at least one pharmaceutically acceptable carrier, diluent or excipient.

5. The recombinant virus vaccine according to claim 4, wherein said Newcastle disease virus gene is a gene coding for hemagglutinin and neuraminidase of Newcastle disease virus.

6. The recombinant virus vaccine according to claim 4, wherein said avian infectious bronchitis virus gene is a spike protein gene of avian infectious bronchitis virus.

7. A method for producing a recombinant virus vaccine which comprises:

(1) culturing in an avian cell culture a recombinant virus comprising the genomic DNA of an attenuated virus of Marek's disease or a herpes virus of turkeys and at least one foreign gene selected from the group consisting of a Newcastle disease virus gene and an avian infectious bronchitis virus gene, wherein said attenuated virus of Marek's disease or said herpes virus of turkeys is selected from the group consisting of a Marek's disease virus BIKEN "C2" strain and a herpes virus of turkeys BIKEN "O1" strain, each respectively having a glycoprotein A antigen gene represented by one of the entire nucleotide sequences shown in FIGS. 3($a$) through 3($k$) hereof, and wherein said foreign gene is operably linked in a correct reading frame of said genomic DNA downstream of a promoter of a glycoprotein A antigen gene of said genomic DNA, wherein said recombinant virus elicits a protective host immune response to infection with Marek's disease virus, to thereby multiply said recombinant virus and simultaneously expressing said foreign gene;

(2) isolating from said avian cell culture the multiplied recombinant virus also containing a polypeptide produced by the expression of said foreign gene; and (3) adding to the isolated recombinant virus at least one pharmaceutically acceptable carrier, diluent or excipient.

8. The method according to claim 7, wherein said Newcastle disease virus gene is a gene coding for hemagglutinin and neuraminidase of Newcastle disease virus.

9. The method according to claim 7, wherein said avian infectious bronchitis virus gene is a spike protein gene of avian infectious bronchitis virus.

10. The method according to claim 7, further comprising, after step (3), subjecting the resultant mixture to lyophilization.

* * * * *